US010286029B2

(12) United States Patent
Awni et al.

(10) Patent No.: US 10,286,029 B2
(45) Date of Patent: May 14, 2019

(54) METHOD FOR TREATING HCV

(71) Applicant: AbbVie Inc., North Chicago, IL (US)

(72) Inventors: Walid M. Awni, Green Oaks, IL (US); Barry M. Bernstein, Mequon, WI (US); Andrew L. Campbell, Lake Forest, IL (US); Sandeep Dutta, Lincolnshire, IL (US); Chih-Wei Lin, Vernon Hills, IL (US); Wei Liu, Mundelein, IL (US); Rajeev M. Menon, Buffalo Grove, IL (US); Thomas J. Podsadecki, Chicago, IL (US); Tianli Wang, Lake Bluff, IL (US); Sven Mensing, Mannheim (DE)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/676,370

(22) Filed: Apr. 1, 2015

(65) Prior Publication Data

US 2015/0283198 A1 Oct. 8, 2015
US 2016/0317602 A9 Nov. 3, 2016

Related U.S. Application Data

(63) Continuation-in-part of application No. 14/210,870, filed on Mar. 14, 2014, now abandoned.

(60) Provisional application No. 61/783,376, filed on Mar. 14, 2013, provisional application No. 62/016,459, filed on Jun. 24, 2014, provisional application No. 61/989,951, filed on May 7, 2014, provisional application No. 61/973,929, filed on Apr. 2, 2014.

(51) Int. Cl.
*A61K 38/06* (2006.01)
*A61K 31/7072* (2006.01)
*A61K 38/05* (2006.01)
*A61K 31/454* (2006.01)
*A61K 31/498* (2006.01)

(52) U.S. Cl.
CPC ............ *A61K 38/06* (2013.01); *A61K 31/454* (2013.01); *A61K 31/498* (2013.01); *A61K 31/7072* (2013.01); *A61K 38/05* (2013.01)

(58) Field of Classification Search
None
See application file for complete search history.

(56) References Cited

U.S. PATENT DOCUMENTS

| 3,466,159 | A | 9/1969 | Abe et al. |
| 3,492,386 | A | 1/1970 | Tsuneo et al. |
| 3,648,037 | A | 3/1972 | Walter, Jr. |
| 3,680,106 | A | 7/1972 | Thomas |
| 3,685,984 | A | 8/1972 | Gilbert et al. |
| 3,809,265 | A | 5/1974 | Krenke et al. |
| 3,853,176 | A | 12/1974 | Henrich |
| 3,937,150 | A | 2/1976 | Miericke et al. |
| 8,466,159 | B2 | 6/2013 | Bernstein et al. |
| 8,492,386 | B2 | 7/2013 | Bernstein et al. |
| 8,648,037 | B2 | 2/2014 | Or et al. |
| 8,680,106 | B2 | 3/2014 | Bernstein et al. |
| 8,685,984 | B2 | 4/2014 | Bernstein et al. |
| 8,809,265 | B2 | 8/2014 | Bernstein et al. |
| 8,853,176 | B2 | 10/2014 | Bernstein et al. |
| 8,937,150 | B2 | 1/2015 | Degoey et al. |
| 8,969,357 | B2 | 3/2015 | Bernstein et al. |
| 8,993,578 | B2 | 3/2015 | Bernstein et al. |
| 2012/0004196 | A1 | 1/2012 | Degoey et al. |
| 2012/0070416 | A1 | 3/2012 | Or et al. |
| 2012/0220562 | A1 | 8/2012 | Degoey et al. |
| 2013/0102026 | A1 | 4/2013 | Borody |
| 2013/0102525 | A1 | 4/2013 | Bernstein et al. |
| 2013/0102526 | A1 | 4/2013 | Bernstein et al. |
| 2013/0102557 | A1 | 4/2013 | Bernstein et al. |
| 2013/0102558 | A1 | 4/2013 | Bernstein et al. |
| 2014/0024579 | A1 | 1/2014 | Bernstein et al. |
| 2014/0057835 | A1 | 2/2014 | Bernstein et al. |
| 2014/0080868 | A1 | 3/2014 | Ng et al. |
| 2014/0080869 | A1 | 3/2014 | Krishnan et al. |
| 2014/0107016 | A1 | 4/2014 | Bernstein et al. |
| 2014/0107017 | A1 | 4/2014 | Bernstein et al. |
| 2014/0275099 | A1 | 9/2014 | Bernstein et al. |
| 2014/0323395 | A1 | 10/2014 | Bernstein et al. |
| 2015/0004196 | A1 | 1/2015 | Perricone |

(Continued)

FOREIGN PATENT DOCUMENTS

| EP | 2583677 A2 | 4/2013 |
| WO | WO-2012040167 A1 | 3/2012 |

(Continued)

OTHER PUBLICATIONS

Franciscus, HCSP fact sheet, download online on Jul. 1, 2015 from URL:<www.hcvadvocate.org>.*
Walpole et al. (BMC Public Health 2012, 12:439).*
Einav S., et al., "The Hepatitis C Virus (HCV) Ns4b RNA Binding Inhibitor Clemizole is Highly Synergistic with HCV Protease Inhibitors," The Journal of Infectious Diseases, 2010, vol. 202 (1), pp. 65-74.
European Association for the Study of the Liver, "EASL Clinical Practice Guidelines: Management of Hepatitis C Virus Infection," Journal of Hepatology, 2011, vol. 55 (2), pp. 245-264.
Grünberger C., et al., "3-Drug Synergistic Interaction of Small Molecular Inhibitors of Hepatitis C Virus Replication," Journal of Infectious Diseases, Journal of Infectious Diseases, 2008, vol. 197, pp. 42-45.

(Continued)

*Primary Examiner* — Sergio Coffa

(57) ABSTRACT

The present invention features interferon-free therapies for the treatment of HCV. Preferably, the treatment is over a shorter duration of treatment, such as no more than 12 weeks. In one aspect, the treatment comprises administering at least two direct acting antiviral agents to a subject with HCV infection, wherein the treatment lasts for 12 weeks and does not include administration of either interferon or ribavirin, and said at least two direct acting antiviral agents comprise (a) Compound 1 or a pharmaceutically acceptable salt thereof and (b) Compound 2 or a pharmaceutically acceptable salt thereof.

34 Claims, 9 Drawing Sheets

(56) References Cited

U.S. PATENT DOCUMENTS

| | | |
|---|---|---|
| 2015/0024999 A1 | 1/2015 | Awni et al. |
| 2015/0196615 A1 | 7/2015 | Awni et al. |
| 2015/0283198 A1 | 10/2015 | Awni et al. |
| 2017/0088583 A1 | 3/2017 | Or et al. |
| 2017/0157104 A1 | 6/2017 | Bellizzi et al. |

FOREIGN PATENT DOCUMENTS

| | | |
|---|---|---|
| WO | WO-2012051361 A1 | 4/2012 |
| WO | WO-2012116257 A1 | 8/2012 |
| WO | 2014047039 A1 | 3/2014 |
| WO | WO-2014047046 A1 | 3/2014 |
| WO | WO-2014099908 A1 | 6/2014 |
| WO | 2014152514 A1 | 9/2014 |
| WO | WO-2015061742 A2 | 4/2015 |
| WO | WO-2015153792 A1 | 10/2015 |
| WO | WO-2015153793 A1 | 10/2015 |
| WO | WO-2017007934 A1 | 1/2017 |

OTHER PUBLICATIONS

International Search Report and Written Opinion for Application No. PCT/US2014/027556, dated Jul. 2, 2014, 10 pages.
International Search Report for Application No. PCT/US2014/027423, dated Jun. 4, 2014, 3 pages.
Koev G., et al., "Antiviral Interactions of an HCV Polymerase Inhibitor with an HCV Protease Inhibitor or Interferon in Vitro," Antiviral Research, 2007, vol. 73 (1), pp. 78-81.
Lawitz E., et al., "A Phase 2a Trial of 12-Week Interferon-Free Therapy with Two Direct-Acting Antivirals (ABT-450/r, ABT-072) and Ribavirin in IL28B C/C Patients with Chronic Hepatitis C Genotype 1," Journal of Hepatology, 2013, vol. 19 (1), pp. 18-23.
Legrand-Abravanel F., et al., "Hepatitis C Virus Genotype 5: Epidemiological Characteristics and Sensitivity to Combination Therapy with Interferon-Alpha Plus Ribavirin," The Journal of Infectious Diseases, 2004, vol. 189 (8), pp. 1397-1400.
Prichard M.N., et al., "A Three-Dimensional Model to Analyze Drug-Drug Interactions," Antiviral Research, 1990, vol. 14 (4-5), pp. 181-206.
Tanabe Y., et al., "Synergistic Inhibition of Intracellular Hepatitis C Virus Replication by Combination of Ribavirin and Interferon-a," The Journal of Infectious Diseases, 2004, vol. 189 (7), pp. 1129-1139.
Wyles D.L., et al., "Synergy of Small Molecular Inhibitors of Hepatitis C Virus Replication Directed at Multiple Viral Targets," Journal of Virology, 2007, vol. 81 (6), pp. 3005-3008.
U.S. Appl. No. 14/210,858.
U.S. Appl. No. 14/210,870.
International Search Report and Written Opinion for Application No. PCT/US2015/023923, dated May 15, 2015, 10 pages.
Lok A., et al., "Combination Therapy With BMS-790052 and BMS-650032 Alone or With Pegylated Interferon and Ribavirin (pegIFN/RBV) Results in Undetectable HCV RNA Through 12 Weeks of Therapy in HCV Genotype 1 Null Responders", Hepatology, John Wiley & Sons, Inc., USA, vol. 52, No. 4, suppl, Oct. 1, 2010, p. 877A, XP009165656; ISSN: 0270-9139.
*Gilead Sciences, Inc. et al. v. Abbott Laboratories, Inc. et al.* Case No. 13-2034, U.S. District Court for the District of Delaware. Order Construing the Terms of U.S. Pat. Nos. 8,466,159 & 8,492,386. Dated Nov. 3, 2015.
Extended European Search Report for Application Np. EP18156337, dated Jun. 15, 2018, 7 pages.
European search report for Application No. EP17196993, dated May 8, 2018, 9 pages.
FDA Guideline for Submitting Supporting Documentation TM8-TM14 (filed with response to Notice of Opposition) in Advancing Health through Innovation, 2017 New Drug Therapy Approvals, 2017, 102 pages.
International Search Report and Written Opinion for Application No. PCT/US2015/023923, dated May 19, 2015, 10 pages.
International Search Report and Written Opinion for Application No. PCT/US2016/041334, dated Oct. 24, 2016, 9 pages.
Jules Levin: "Magellan-2: Safety and Efficacy of Glecaprevir/Pibrentasvir in Liver or Renal Transplant Adults With Chronic Hepatitis C Genotype 1-6 Infection", Apr. 22, 2017 (Apr. 22, 2017), XP055466892, Retreived from the Internet: URL:http://www.natap.org/2017/EASL/EASL_32.htm [retrieved on Apr. 12, 2018].
Lawitz E.J., et al., "Potent Antiviral Activities of the Direct-Acting Antivirals ABT-493 and ABT-530 with Three-Day Monotherapy for Hepatitis C Virus Genotype 1 Infection," Antimicrobial Agents and Chemotherapy, Dec. 28, 2015, vol. 60(3), pp. 1546-1555.
Lok A., et al., Combination Therapy With BMS-790052 and BMS-650032 Alone or With Pegylated Interferon and Ribavirin (pegIFN/RBV) Results in Undetectable HCV RNA Through 12 Weeks of Therapy in HCV Genotype 1 Null Responders, 61th Annual Meeting of the American Association for the Study of Liver Diseases Boston, MA, Oct. 30-Nov. 3, 2010. Retrieved from the Internet: URL: http://www.natap.org/2010/AASLD/AASLD_16.htm.
Franciscus, HCSP Fact Sheet, [online] [Retreived on Apr. 12, 2018]. Retreived from the Internet:<url:< a="" href="http://www.hcvadvocate.org">www.hcvadvocate.org</url:>.
Notice of Opposition for European Patent No. EP14719977.2 mailed on Jan. 25, 2010, 151 pages.
Response to Notice of Opposition for European Patent No. EP2968301 dated Jun. 18, 2018, 18 pages.
Gane, E., et al., "High Efficacy of ABT-493 and ABT-530 Treatment in Patients With HCV Genotype 1 or 3 Infection and Compensated Cirrhosis," Gastroenterology, Oct. 2016, vol. 151 (4), pp. 651-659.
Kwo, P.Y., et al., "Glecaprevir and Pibrentasvir Yield High Response Rates in Patients With HCV Genotype 1-6 Without Cirrhosis," Journal of Hepatology, Aug. 2017, vol. 67 (2), pp. 263-271.
Mendizabal, M., et al., "Chronic Hepatitis C and Chronic Kidney Disease: Advances, Limitations and Unchartered Territories," Journal of Viral Hepatitis, Jun. 2017, vol. 24 (6), pp. 442-453.
Poordad, F., et al., "Glecaprevir and Pibrentasvir for 12 Weeks for Hepatitis C Virus Genotype 1 Infection and Prior Direct-acting Antiviral Treatment," Hepatology, Aug. 2017, vol. 66 (2), pp. 389-397.
Reau N., et al., "Magellan-2: Safety and Efficacy of Glecaprevir/pibrentasvir in Liver or Renal Transplant Adults with Chronic Hepatitis C Genotype 1-6 Infection," Journal of Hepatology, Apr. 2017, vol. 66 (1), pp. S90-S91.
Verna, E.C., et al., "HCV Antiviral Therapy in Liver Transplant Candidates and Recipients With Renal Insufficiency," Transplantation, May 2017, vol. 101 (5), pp. 924-932.
Cortesi P.A., et al., "Cost-Effectiveness of New Direct-Acting Antivirals to Prevent Post-Liver Transplant Recurrent Hepatitis," American Journal of Transplantation, Jul. 2015, vol. 15 (7), pp. 1817-1826.
Dore G.J.,"The Changing Therapeutic Landscape for Hepatitis C," The Medical Journal of Australia, Jun. 2012, vol. 196 (10), pp. 629-632.
Herbst D.A., et al., "Sofosbuvir, a Nucleotide Polymerase Inhibitor, for the Treatment of Chronic Hepatitis C Virus Infection," Expert opinion on investigational drugs, Apr. 2013, vol. 22(4), pp. 527-536.
Latwitz et al., "Potent Antiviral Activities of the Direct-Acting Antivirals ABT-493 and ABT-530 with Three-Day Monotherapy for Hepatitis C Virus Genotype 1 Infection," Antimicrob Agents Chemother, Dec. 2015, vol. 60 (3), pp. 1546-1555.
Levin J., ABT-493, A Potent HCV NS3/4A Protease Inhibitor with Broad Genotype Coverage, 21st Conference on Retroviruses and Opportunistic Infections Boston, MA, Mar. 3-6, 2014, 9 pages.
Notice of Opposition dated Jun. 22, 2018 for European Patent EP2968302.
Notice of Opposition dated Jan. 21, 2019 for European Patent EP2968301.
Response to Opposition dated Feb. 11, 2019 for European Patent EP2968301.

\* cited by examiner

METHOD FOR TREATING HCV

This application claims the benefit of U.S. Provisional Application No. 61/973,929 filed Apr. 2, 2014, U.S. Provisional Application No. 61/989,951 filed May 7, 2014, and U.S. Provisional Application No. 62/016,459 filed Jun. 24, 2014, all of which are incorporated herein by reference in their entireties. This application is also a continuation-in-part of U.S. patent application Ser. No. 14/210,870 filed Mar. 14, 2014, which claims the benefit of U.S. Provisional Application No. 61/783,376 filed Mar. 14, 2013.

FIELD OF THE INVENTION

The present invention relates to interferon- and ribavirin-free treatment for hepatitis C virus (HCV).

BACKGROUND OF THE INVENTION

The HCV is an RNA virus belonging to the Hepacivirus genus in the Flaviviridae family. The enveloped HCV virion contains a positive stranded RNA genome encoding all known virus-specific proteins in a single, uninterrupted, open reading frame. The open reading frame comprises approximately 9500 nucleotides and encodes a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B.

Chronic HCV infection is associated with progressive liver pathology, including cirrhosis and hepatocellular carcinoma. Chronic hepatitis C may be treated with peginterferon-alpha in combination with ribavirin. Substantial limitations to efficacy and tolerability remain as many users suffer from side effects, and viral elimination from the body is often incomplete. Therefore, there is a need for new therapies to treat HCV infection.

BRIEF SUMMARY OF THE INVENTION

One aspect of the present invention features methods for treating HCV infection in a subject in need of such treatment. The methods comprise administering at least two direct acting antiviral agents (DAAs) to the subject for a duration of no more than 12 weeks, or for another duration as set forth herein. The at least two DAAs comprise Compound 1 (or a pharmaceutically acceptable salt thereof) and Compound 2 (or a pharmaceutically acceptable salt thereof); and the at least two DAAs can also additionally comprise one or more other DAAs, such as sofosbuvir or another HCV polymerase inhibitor. Preferably, the duration of the treatment is 12 weeks. The duration of the treatment can also last for less than 12 weeks; for example, the duration can last for 11, 10, 9, 8, 7, 6, 5 or 4 weeks, or no more than 8 weeks. Where three or more DAAs are used in the treatment regimen, the duration of the treatment preferably lasts for no more than 8 weeks; for example, the duration can last for 8, 7, 6, 5 or 4 weeks. Preferably, the two or more DAAs are administered in amounts effective to provide a sustained virological response (SVR) or achieve another desired measure of effectiveness in the subject. The subject is not administered either interferon or ribavirin during the treatment regimen. Put another way, the methods exclude the administration of interferon and ribavirin to the subject, thereby avoiding the side effects associated with interferon or ribavirin.

Another aspect of the present invention features methods for treating a population of subjects having HCV infection. The methods comprise administering at least two DAAs to the subjects for a duration of no more than 12 weeks, such as for a duration of 12, 11, 10, 9, 8, 7, 6, 5 or 4 weeks, or no more than 8 weeks. The at least two DAAs comprise Compound 1 (or a pharmaceutically acceptable salt thereof) and Compound 2 (or a pharmaceutically acceptable salt thereof); and the at least two DAAs can also additionally comprise one or more other DAAs, such as sofosbuvir or another HCV polymerase inhibitor. Preferably, the at least two DAAs are administered to the subjects in amounts effective to result in SVR or another measure of effectiveness in at least about 70% of the population, preferably at least about 80% of the population, or more preferably at least about 90% of the population.

In any method described herein, the at least two DAAs comprise (a) Compound 1 or a pharmaceutically acceptable salt thereof, and (b) Compound 2 or a pharmaceutically acceptable salt thereof. The at least two DAAs can also optionally comprise one or more other anti-HCV agents. These other optional anti-HCV agents can be selected from protease inhibitors, nucleoside or nucleotide polymerase inhibitors, non-nucleoside polymerase inhibitors, NS3B inhibitors, NS4A inhibitors, NS5A inhibitors, NS5B inhibitors, cyclophilin inhibitors, or combinations thereof. Non-limiting examples of the other optional antic-HCV agents include PSI-7977 (sofosbuvir), PSI-938, BMS-790052 (daclatasvir), BMS-650032 (asunaprevir), BMS-791325, GS-5885 (ledipasvir), GS-9451 (tegobuvir), GS-9190, GS-9256, BI-201335, BI-27127, telaprevir, VX-222, TMC-435 (simeprevir), MK-5172, MK-7009 (vaniprevir), danoprevir, R7128 (mericitabine), and any combination thereof.

For example, the DAAs used in a method of the present invention can comprise or consist of (a) Compound 1 or a pharmaceutically acceptable salt thereof, and (b) Compound 2 or a pharmaceutically acceptable salt thereof. For another example, the DAAs used in a method of the present invention can comprise or consist of (a) Compound 1 or a pharmaceutically acceptable salt thereof, (b) Compound 2 or a pharmaceutically acceptable salt thereof, and (c) a HCV polymerase inhibitor, wherein said HCV polymerase inhibitor can be a nucleotide or nucleoside polymerase inhibitor or a non-nucleoside or non-nucleotide polymerase inhibitor. For yet another example, the DAAs used in a method of the present invention can comprise or consist of (a) Compound 1 or a pharmaceutically acceptable salt thereof, (b) Compound 2 or a pharmaceutically acceptable salt thereof, and (c) a nucleotide or nucleoside HCV polymerase inhibitor. For yet another example, the DAAs used in a method of the present invention can comprise or consist of (a) Compound 1 or a pharmaceutically acceptable salt thereof, (b) Compound 2 or a pharmaceutically acceptable salt thereof, and (c) sofosbuvir. For yet another example, the DAAs used in a method of the present invention can comprise or consist of (a) Compound 2 or a pharmaceutically acceptable salt thereof and (b) sofosbuvir.

In any method described herein, the DAAs can be administered in any effective dosing schemes and/or frequencies; for example, they can each be administered daily. Each DAA can be administered either separately or in combination, and each DAA can be administered once a day, twice a day, or three times a day. Preferably, Compound 1 (or a pharmaceutically acceptable salt thereof) and Compound 2 (or a pharmaceutically acceptable salt thereof) are administered once daily.

Preferably, Compound 1 (or a pharmaceutically acceptable salt thereof) is administered from 100 mg to 600 mg once daily, and Compound 2 (or a pharmaceutically acceptable salt thereof) is administered from 50 to 500 mg once daily. More preferably, Compound 1 (or a pharmaceutically acceptable salt thereof) is administered from 200 mg to 600 mg once daily, and Compound 2 (or a pharmaceutically acceptable salt thereof) is administered from 100 to 500 mg once daily. Highly preferably, Compound 1 (or a pharmaceutically acceptable salt thereof) is administered from 400 mg to 600 mg once daily, and Compound 2 (or a pharmaceutically acceptable salt thereof) is administered from 100 to 500 mg once daily. It was unexpectedly found that 200-300 mg Compound 1 has comparable anti-HCV efficacy to 400 mg Compound 1. Therefore, more preferably, Compound 1 (or a pharmaceutically acceptable salt thereof) is administered from 200 mg to 300 mg once daily, and Compound 2 (or a pharmaceutically acceptable salt thereof) is administered from 100 to 500 mg once daily. For example, Compound 1 (or a pharmaceutically acceptable salt thereof) can be administered 200 mg once daily, and Compound 2 (or a pharmaceutically acceptable salt thereof) is administered 120 mg once daily. For another example, Compound 1 (or a pharmaceutically acceptable salt thereof) can be administered 300 mg once daily, and Compound 2 (or a pharmaceutically acceptable salt thereof) is administered 120 mg once daily. For yet another example, Compound 1 (or a pharmaceutically acceptable salt thereof) can be administered 400 mg once daily, and Compound 2 (or a pharmaceutically acceptable salt thereof) is administered 120 mg once daily. For another example, Compound 1 (or a pharmaceutically acceptable salt thereof) can be administered 400 mg once daily, and Compound 2 (or a pharmaceutically acceptable salt thereof) can be administered 240 mg once daily.

In yet another aspect, the present invention features a combination of Compound 1 (or a pharmaceutically acceptable salt thereof) and Compound 2 (or a pharmaceutically acceptable salt thereof) for use to treat HCV infection. The treatment comprises administering the DAAs to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment does not include administering interferon or ribavirin (i.e., neither interferon nor ribavirin are administered). Compound 1 (or the salt thereof) and Compound 2 (or the salt thereof) can be administered concurrently or sequentially. Preferably, Compound 1 (or the salt thereof) and Compound 2 (or the salt thereof) can be administered once daily. As a non-limiting example, the patient being treated is infected with HCV genotype 1, such as genotype 1a or 1b. As another non-limiting example, the patient is infected with HCV genotype 2. As another non-limiting example, the patient is infected with HCV genotype 3. As another non-limiting example, the patient is infected with HCV genotype 4. As another non-limiting example, the patient is infected with HCV genotype 5. As another non-limiting example, the patient is infected with HCV genotype 6. As yet another non-limiting example, the patient is a HCV-treatment naïve patient, a HCV-treatment experienced patient, an interferon non-responder (e.g., a null responder), or not a candidate for interferon treatment. As used in this application, the interferon non-responder patients include partial interferon responders and interferon rebound patients. See GUIDANCE FOR INDUSTRY—CHRONIC HEPATITIS C VIRUS INFECTION: DEVELOPING DIRECT-ACTING ANTIVIRAL AGENTS FOR TREATMENT (FDA, September 2010, draft guidance) for the definitions of naive, partial responder, responder relapser (i.e., rebound), and null responder patients. The interferon non-responder patients also include null responder patients. In one example of this aspect of the invention, the treatment lasts for 12 weeks, and the subject being treated is a naïve patient infected with HCV genotype 1. In another example, the treatment lasts for 11 weeks, and the subject being treated is a naïve patient infected with HCV genotype 1. In still another example, the treatment lasts for 10 weeks, and the subject being treated is a naïve patient infected with HCV genotype 1. In yet another example, the treatment lasts for 9 weeks, and the subject being treated is a naïve patient infected with HCV genotype 1. In yet another example, the treatment lasts for 8 weeks, and the subject being treated is a naïve patient infected with HCV genotype 1. In yet another example, the treatment lasts for 7 weeks, and the subject being treated is a naïve patient infected with HCV genotype 1. In yet another example, the treatment lasts for 6 weeks, and the subject being treated is a naïve patient infected with HCV genotype 1. In yet another example, the treatment lasts for 5 weeks, and the subject being treated is a naïve patient infected with HCV genotype 1. In yet another example, the treatment lasts for 4 weeks, and the subject being treated is a naïve patient infected with HCV genotype 1. In yet another example, the treatment lasts for 12 weeks, and the subject being treated is a naïve patient infected with HCV genotype 3. In another example, the treatment lasts for 11 weeks, and the subject being treated is a naïve patient infected with HCV genotype 3. In still another example, the treatment lasts for 10 weeks, and the subject being treated is a naïve patient infected with HCV genotype 3. In yet another example, the treatment lasts for 9 weeks, and the subject being treated is a naïve patient infected with HCV genotype 3. In yet another example, the treatment lasts for 8 weeks, and the subject being treated is a naïve patient infected with HCV genotype 3. In yet another example, the treatment lasts for 7 weeks, and the subject being treated is a naïve patient infected with HCV genotype 3. In yet another example, the treatment lasts for 6 weeks, and the subject being treated is a naïve patient infected with HCV genotype 3. In yet another example, the treatment lasts for 5 weeks, and the subject being treated is a naïve patient infected with HCV genotype 3. In yet another example, the treatment lasts for 4 weeks, and the subject being treated is a naïve patient infected with HCV genotype 3. In yet another example, the treatment lasts for 12 weeks, and the subject being treated is a non-responder (e.g., a null responder) infected with HCV genotype 1. In another example, the treatment lasts for 11 weeks, and the subject being treated is a non-responder (e.g., a null responder) infected with HCV genotype 1. In still another example, the treatment lasts for 10 weeks, and the subject being treated is a non-responder (e.g., a null responder) infected with HCV genotype 1. In yet another example, the treatment lasts for 9 weeks, and the subject being treated is a non-responder (e.g., a null responder) infected with HCV genotype 1. In yet another example, the treatment lasts for 8 weeks, and the subject being treated is a non-responder (e.g., a null responder) infected with HCV genotype 1. In yet another example, the treatment lasts for 7 weeks, and the subject being treated is a non-responder (e.g., a null responder) infected with HCV genotype 1. In yet another example, the treatment lasts for 6 weeks, and the subject being treated is a non-responder (e.g., a null responder) infected with HCV genotype 1. In yet another example, the treatment lasts for 5 weeks, and the subject being treated is a non-responder (e.g., a null responder) infected with HCV genotype 1. In yet another example, the treatment lasts for 4 weeks, and the subject being treated is a non-responder (e.g., a null responder) infected with HCV genotype 1. In yet another example, the treatment lasts for 12 weeks, and the subject being treated is a non-responder (e.g., a null responder) infected with HCV genotype 3. In another example, the treatment lasts for 11 weeks, and the subject being treated is a non-responder (e.g., a null responder) infected with HCV genotype 3. In still another example, the treatment lasts for 10 weeks, and the subject being treated is a non-responder (e.g., a null responder) infected with HCV genotype 3. In yet another example, the treatment lasts for 9 weeks, and the subject being treated is a non-responder (e.g., a null responder) infected with HCV genotype 3. In yet another example, the treatment lasts for 8 weeks, and the subject being treated is a non-responder (e.g., a null responder) infected with HCV genotype 3. In yet another example, the treatment lasts for 7 weeks, and the subject being treated is a non-responder (e.g., a null responder) infected with HCV genotype 3. In yet another example, the treatment lasts for 6 weeks, and the subject being treated is a non-responder (e.g., a null responder) infected with HCV genotype 3. In yet another example, the treatment lasts for 5 weeks, and the subject being treated is a non-responder (e.g., a null responder) infected with HCV genotype 3. In yet another example, the treatment lasts for 4 weeks, and the subject being treated is a non-responder (e.g., a null responder) infected with HCV genotype 3.

In yet another aspect, the present invention features a combination of Compound 1 (or a pharmaceutically acceptable salt thereof), Compound 2 (or a pharmaceutically acceptable salt thereof), and an HCV polymerase inhibitor for use to treat HCV infection. The treatment comprises administering the DAAs to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment does not include administering either interferon or ribavirin, i.e., neither interferon nor ribavirin are administered. Compound 1 (or the salt thereof), Compound 2 (or the salt thereof) and the HCV polymerase inhibitor can be administered concurrently or sequentially. Preferably, Compound 1 (or the salt thereof), Compound 2 (or the salt thereof) and the HCV polymerase inhibitor can be administered once daily. As a non-limiting example, the patient being treated is infected with HCV genotype 1, such as genotype 1a or 1b. As another non-limiting example, the patient is infected with HCV genotype 2. As another non-limiting example, the patient is infected with HCV genotype 3. As another non-limiting example, the patient is infected with HCV genotype 4. As another non-limiting example, the patient is infected with HCV genotype 5. As another non-limiting example, the patient is infected with HCV genotype 6. As yet another non-limiting example, the patient is a HCV-treatment naïve patient, a HCV-treatment experienced patient, an interferon non-responder (e.g., a null responder), or not a candidate for interferon treatment. In one example of this aspect of the invention, the treatment lasts for 12 weeks, and the subject being treated is a naïve patient infected with HCV genotype 1. In another example, the treatment lasts for 11 weeks, and the subject being treated is a naïve patient infected with HCV genotype 1. In still another example, the treatment lasts for 10 weeks, and the subject being treated is a naïve patient infected with HCV genotype 1. In yet another example, the treatment lasts for 9 weeks, and the subject being treated is a naïve patient infected with HCV genotype 1. In yet another example, the treatment lasts for 8 weeks, and the subject being treated is a naïve patient infected with HCV genotype 1. In yet another example, the treatment lasts for 7 weeks, and the subject being treated is a naïve patient infected with HCV genotype 1. In yet another example, the treatment lasts for 6 weeks, and the subject being treated is a naïve patient infected with HCV genotype 1. In yet another example, the treatment lasts for 5 weeks, and the subject being treated is a naïve patient infected with HCV genotype 1. In yet another example, the treatment lasts for 4 weeks, and the subject being treated is a naïve patient infected with HCV genotype 1. In yet another example, the treatment lasts for 12 weeks, and the subject being treated is a naïve patient infected with HCV genotype 3. In another example, the treatment lasts for 11 weeks, and the subject being treated is a naïve patient infected with HCV genotype 3. In still another example, the treatment lasts for 10 weeks, and the subject being treated is a naïve patient infected with HCV genotype 3. In yet another example, the treatment lasts for 9 weeks, and the subject being treated is a naïve patient infected with HCV genotype 3. In yet another example, the treatment lasts for 8 weeks, and the subject being treated is a naïve patient infected with HCV genotype 3. In yet another example, the treatment lasts for 7 weeks, and the subject being treated is a naïve patient infected with HCV genotype 3. In yet another example, the treatment lasts for 6 weeks, and the subject being treated is a naïve patient infected with HCV genotype 3. In yet another example, the treatment lasts for 5 weeks, and the subject being treated is a naïve patient infected with HCV genotype 3. In yet another example, the treatment lasts for 4 weeks, and the subject being treated is a naïve patient infected with HCV genotype 3. In yet another example, the treatment lasts for 12 weeks, and the subject being treated is a non-responder (e.g., a null responder) infected with HCV genotype 1. In another example, the treatment lasts for 11 weeks, and the subject being treated is a non-responder (e.g., a null responder) infected with HCV genotype 1. In still another example, the treatment lasts for 10 weeks, and the subject being treated is a non-responder (e.g., a null responder) infected with HCV genotype 1. In yet another example, the treatment lasts for 9 weeks, and the subject being treated is a non-responder (e.g., a null responder) infected with HCV genotype 1. In yet another example, the treatment lasts for 8 weeks, and the subject being treated is a non-responder (e.g., a null responder) infected with HCV genotype 1. In yet another example, the treatment lasts for 7 weeks, and the subject being treated is a non-responder (e.g., a null responder) infected with HCV genotype 1. In yet another example, the treatment lasts for 6 weeks, and the subject being treated is a non-responder (e.g., a null responder) infected with HCV genotype 1. In yet another example, the treatment lasts for 5 weeks, and the subject being treated is a non-responder (e.g., a null responder) infected with HCV genotype 1. In yet another example, the treatment lasts for 4 weeks, and the subject being treated is a non-responder (e.g., a null responder) infected with HCV genotype 1. In yet another example, the treatment lasts for 12 weeks, and the subject being treated is a non-responder (e.g., a null responder) infected with HCV genotype 3. In another example, the treatment lasts for 11 weeks, and the subject being treated is a non-responder (e.g., a null responder) infected with HCV genotype 3. In still another example, the treatment lasts for 10 weeks, and the subject being treated is a non-responder (e.g., a null responder) infected with HCV genotype 3. In yet another example, the treatment lasts for 9 weeks, and the subject being treated is a non-responder (e.g., a null responder) infected with HCV genotype 3. In yet another example, the treatment lasts for 8 weeks, and the subject being treated is a non-responder (e.g., a null responder) infected with HCV genotype 3. In yet another example, the treatment lasts for 7 weeks, and the subject being treated is a non-responder (e.g., a null responder) infected with HCV genotype 3. In yet another example, the treatment lasts for 6 weeks, and the subject being treated is a non-responder (e.g., a null responder) infected with HCV genotype 3. In yet another example, the treatment lasts for 5 weeks, and the subject being treated is a non-responder (e.g., a null responder) infected with HCV genotype 3. In yet another example, the treatment lasts for 4 weeks, and the subject being treated is a non-responder (e.g., a null responder) infected with HCV genotype 3.

In yet another aspect, the present invention features a combination of Compound 1 (or a pharmaceutically acceptable salt thereof), Compound 2 (or a pharmaceutically acceptable salt thereof), and sofosbuvir for use to treat HCV infection. The treatment comprises administering the DAAs to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment does not include administering interferon. Compound 1 (or the salt thereof), Compound 2 (or the salt thereof) and sofosbuvir can be administered concurrently or sequentially. Preferably, Compound 1 (or the salt thereof), Compound 2 (or the salt thereof) and sofosbuvir can be administered once daily. As a non-limiting example, the patient being treated is infected with HCV genotype 1, such as genotype 1a or 1b. As another non-limiting example, the patient is infected with HCV genotype 2. As another non-limiting example, the patient is infected with HCV genotype 3. As another non-limiting example, the patient is infected with HCV genotype 4. As another non-limiting example, the patient is infected with HCV genotype 5. As another non-limiting example, the patient is infected with HCV genotype 6. As yet another non-limiting example, the patient is a HCV-treatment naïve patient, a HCV-treatment experienced patient, an interferon non-responder (e.g., a null responder), or not a candidate for interferon treatment. In one example of this aspect of the invention, the treatment lasts for 12 weeks, and the subject being treated is a naïve patient infected with HCV genotype 1. In another example, the treatment lasts for 11 weeks, and the subject being treated is a naïve patient infected with HCV genotype 1. In still another example, the treatment lasts for 10 weeks, and the subject being treated is a naïve patient infected with HCV genotype 1. In yet another example, the treatment lasts for 9 weeks, and the subject being treated is a naïve patient infected with HCV genotype 1. In yet another example, the treatment lasts for 8 weeks, and the subject being treated is a naïve patient infected with HCV genotype 1. In yet another example, the treatment lasts for 7 weeks, and the subject being treated is a naïve patient infected with HCV genotype 1. In yet another example, the treatment lasts for 6 weeks, and the subject being treated is a naïve patient infected with HCV genotype 1. In yet another example, the treatment lasts for 5 weeks, and the subject being treated is a naïve patient infected with HCV genotype 1. In yet another example, the treatment lasts for 4 weeks, and the subject being treated is a naïve patient infected with HCV genotype 1. In yet another example, the treatment lasts for 12 weeks, and the subject being treated is a naïve patient infected with HCV genotype 3. In another example, the treatment lasts for 11 weeks, and the subject being treated is a naïve patient infected with HCV genotype 3. In still another example, the treatment lasts for 10 weeks, and the subject being treated is a naïve patient infected with HCV genotype 3. In yet another example, the treatment lasts for 9 weeks, and the subject being treated is a naïve patient infected with HCV genotype 3. In yet another example, the treatment lasts for 8 weeks, and the subject being treated is a naïve patient infected with HCV genotype 3. In yet another example, the treatment lasts for 7 weeks, and the subject being treated is a naïve patient infected with HCV genotype 3. In yet another example, the treatment lasts for 6 weeks, and the subject being treated is a naïve patient infected with HCV genotype 3. In yet another example, the treatment lasts for 5 weeks, and the subject being treated is a naïve patient infected with HCV genotype 3. In yet another example, the treatment lasts for 4 weeks, and the subject being treated is a naïve patient infected with HCV genotype 3. In yet another example, the treatment lasts for 12 weeks, and the subject being treated is a non-responder (e.g., a null responder) infected with HCV genotype 1. In another example, the treatment lasts for 11 weeks, and the subject being treated is a non-responder (e.g., a null responder) infected with HCV genotype 1. In still another example, the treatment lasts for 10 weeks, and the subject being treated is a non-responder (e.g., a null responder) infected with HCV genotype 1. In yet another example, the treatment lasts for 9 weeks, and the subject being treated is a non-responder (e.g., a null responder) infected with HCV genotype 1. In yet another example, the treatment lasts for 8 weeks, and the subject being treated is a non-responder (e.g., a null responder) infected with HCV genotype 1. In yet another example, the treatment lasts for 7 weeks, and the subject being treated is a non-responder (e.g., a null responder) infected with HCV genotype 1. In yet another example, the treatment lasts for 6 weeks, and the subject being treated is a non-responder (e.g., a null responder) infected with HCV genotype 1. In yet another example, the treatment lasts for 5 weeks, and the subject being treated is a non-responder (e.g., a null responder) infected with HCV genotype 1. In yet another example, the treatment lasts for 4 weeks, and the subject being treated is a non-responder (e.g., a null responder) infected with HCV genotype 1. In yet another example, the treatment lasts for 12 weeks, and the subject being treated is a non-responder (e.g., a null responder) infected with HCV genotype 3. In another example, the treatment lasts for 11 weeks, and the subject being treated is a non-responder (e.g., a null responder) infected with HCV genotype 3. In still another example, the treatment lasts for 10 weeks, and the subject being treated is a non-responder (e.g., a null responder) infected with HCV genotype 3. In yet another example, the treatment lasts for 9 weeks, and the subject being treated is a non-responder (e.g., a null responder) infected with HCV genotype 3. In yet another example, the treatment lasts for 8 weeks, and the subject being treated is a non-responder (e.g., a null responder) infected with HCV genotype 3. In yet another example, the treatment lasts for 7 weeks, and the subject being treated is a non-responder (e.g., a null responder) infected with HCV genotype 3. In yet another example, the treatment lasts for 6 weeks, and the subject being treated is a non-responder (e.g., a null responder) infected with HCV genotype 3. In yet another example, the treatment lasts for 5 weeks, and the subject being treated is a non-responder (e.g., a null responder) infected with HCV genotype 3. In yet another example, the treatment lasts for 4 weeks, and the subject being treated is a non-responder (e.g., a null responder) infected with HCV genotype 3.

In yet another aspect, the present invention features a combination of Compound 2 (or a pharmaceutically acceptable salt thereof) and sofosbuvir for use to treat HCV infection. The treatment comprises administering the DAAs to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment does not include administering interferon. Compound 2 (or the salt thereof) and sofosbuvir can be administered concurrently or sequentially. Preferably, Compound 2 (or the salt thereof) and sofosbuvir can be administered once daily. As a non-limiting example, the patient being treated is infected with HCV genotype 1, such as genotype 1a or 1b. As another non-limiting example, the patient is infected with HCV genotype 2. As another non-limiting example, the patient is infected with HCV genotype 3. As another non-limiting example, the patient is infected with HCV genotype 4. As another non-limiting example, the patient is infected with HCV genotype 5. As another non-limiting example, the patient is infected with HCV genotype 6. As yet another non-limiting example, the patient is a HCV-treatment naïve patient, a HCV-treatment experienced patient, an interferon non-responder (e.g., a null responder), or not a candidate for interferon treatment. In one example of this aspect of the invention, the treatment lasts for 12 weeks, and the subject being treated is a naïve patient infected with HCV genotype 1. In another example, the treatment lasts for 11 weeks, and the subject being treated is a naïve patient infected with HCV genotype 1. In still another example, the treatment lasts for 10 weeks, and the subject being treated is a naïve patient infected with HCV genotype 1. In yet another example, the treatment lasts for 9 weeks, and the subject being treated is a naïve patient infected with HCV genotype 1. In yet another example, the treatment lasts for 8 weeks, and the subject being treated is a naïve patient infected with HCV genotype 1. In yet another example, the treatment lasts for 7 weeks, and the subject being treated is a naïve patient infected with HCV genotype 1. In yet another example, the treatment lasts for 6 weeks, and the subject being treated is a naïve patient infected with HCV genotype 1. In yet another example, the treatment lasts for 5 weeks, and the subject being treated is a naïve patient infected with HCV genotype 1. In yet another example, the treatment lasts for 4 weeks, and the subject being treated is a naïve patient infected with HCV genotype 1. In yet another example, the treatment lasts for 12 weeks, and the subject being treated is a naïve patient infected with HCV genotype 3. In another example, the treatment lasts for 11 weeks, and the subject being treated is a naïve patient infected with HCV genotype 3. In still another example, the treatment lasts for 10 weeks, and the subject being treated is a naïve patient infected with HCV genotype 3. In yet another example, the treatment lasts for 9 weeks, and the subject being treated is a naïve patient infected with HCV genotype 3. In yet another example, the treatment lasts for 8 weeks, and the subject being treated is a naïve patient infected with HCV genotype 3. In yet another example, the treatment lasts for 7 weeks, and the subject being treated is a naïve patient infected with HCV genotype 3. In yet another example, the treatment lasts for 6 weeks, and the subject being treated is a naïve patient infected with HCV genotype 3. In yet another example, the treatment lasts for 5 weeks, and the subject being treated is a naïve patient infected with HCV genotype 3. In yet another example, the treatment lasts for 4 weeks, and the subject being treated is a naïve patient infected with HCV genotype 3. In yet another example, the treatment lasts for 12 weeks, and the subject being treated is a non-responder (e.g., a null responder) infected with HCV genotype 1. In another example, the treatment lasts for 11 weeks, and the subject being treated is a non-responder (e.g., a null responder) infected with HCV genotype 1. In still another example, the treatment lasts for 10 weeks, and the subject being treated is a non-responder (e.g., a null responder) infected with HCV genotype 1. In yet another example, the treatment lasts for 9 weeks, and the subject being treated is a non-responder (e.g., a null responder) infected with HCV genotype 1. In yet another example, the treatment lasts for 8 weeks, and the subject being treated is a non-responder (e.g., a null responder) infected with HCV genotype 1. In yet another example, the treatment lasts for 7 weeks, and the subject being treated is a non-responder (e.g., a null responder) infected with HCV genotype 1. In yet another example, the treatment lasts for 6 weeks, and the subject being treated is a non-responder (e.g., a null responder) infected with HCV genotype 1. In yet another example, the treatment lasts for 5 weeks, and the subject being treated is a non-responder (e.g., a null responder) infected with HCV genotype 1. In yet another example, the treatment lasts for 4 weeks, and the subject being treated is a non-responder (e.g., a null responder) infected with HCV genotype 1. In yet another example, the treatment lasts for 12 weeks, and the subject being treated is a non-responder (e.g., a null responder) infected with HCV genotype 3. In another example, the treatment lasts for 11 weeks, and the subject being treated is a non-responder (e.g., a null responder) infected with HCV genotype 3. In still another example, the treatment lasts for 10 weeks, and the subject being treated is a non-responder (e.g., a null responder) infected with HCV genotype 3. In yet another example, the treatment lasts for 9 weeks, and the subject being treated is a non-responder (e.g., a null responder) infected with HCV genotype 3. In yet another example, the treatment lasts for 8 weeks, and the subject being treated is a non-responder (e.g., a null responder) infected with HCV genotype 3. In yet another example, the treatment lasts for 7 weeks, and the subject being treated is a non-responder (e.g., a null responder) infected with HCV genotype 3. In yet another example, the treatment lasts for 6 weeks, and the subject being treated is a non-responder (e.g., a null responder) infected with HCV genotype 3. In yet another example, the treatment lasts for 5 weeks, and the subject being treated is a non-responder (e.g., a null responder) infected with HCV genotype 3. In yet another example, the treatment lasts for 4 weeks, and the subject being treated is a non-responder (e.g., a null responder) infected with HCV genotype 3.

A treatment regimen of the present invention generally constitutes a complete treatment regimen, i.e., no subsequent interferon-containing regimen is intended. Thus, a treatment or use described herein generally does not include any subsequent interferon-containing or ribavirin-containing treatment.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description

BRIEF DESCRIPTION OF THE DRAWINGS

The drawings are provided for illustration, not limitation.

DETAILED DESCRIPTION OF THE INVENTION

Figure 1:
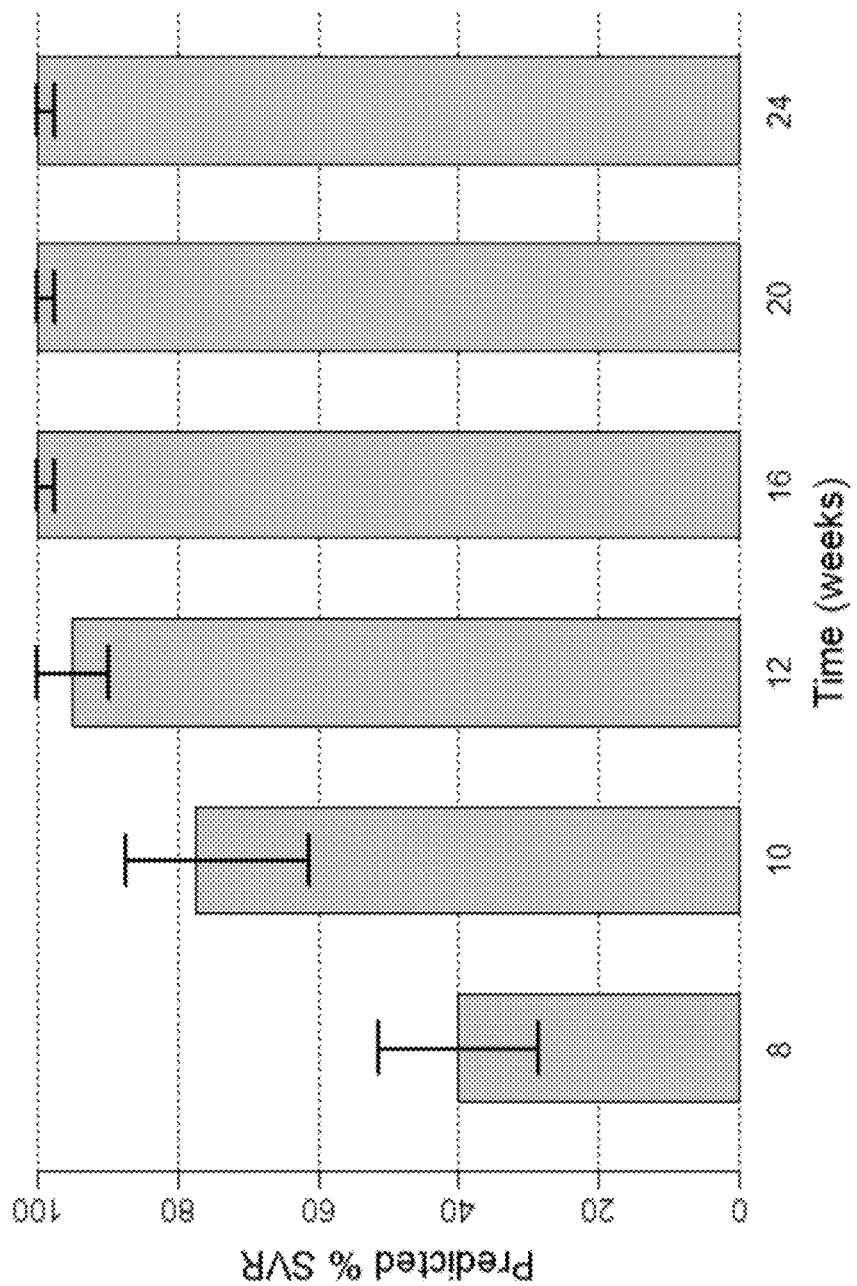
FIG. 1 shows the predicted median SVR percentages and 90% SVR confidence intervals for interferon/ribavirin-free, 2-DAA regimens comprising the use of Compound 1 (400 mg once daily) and Compound 2 (120 mg once daily) to treat genotype 1 naïve subjects.

The methods of the present invention include administering Compound 1 (or a pharmaceutically acceptable salt thereof) and Compound 2 (or a pharmaceutically acceptable salt thereof) to a subject in need thereof. Compound 1 has the following structure:

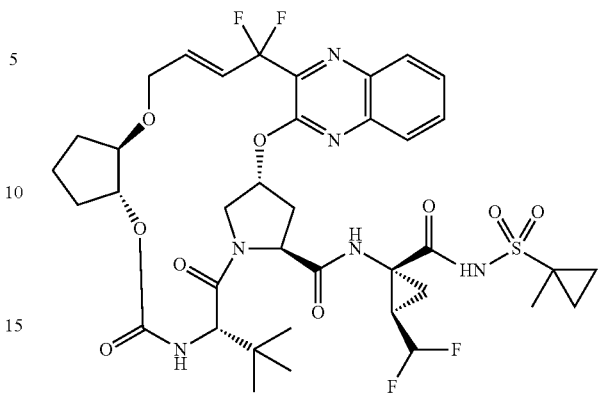

Compound 1 is a potent HCV protease inhibitor and is described in U.S. Patent Application Publication No. 2012/0070416.

Compound 2 has the following structure:

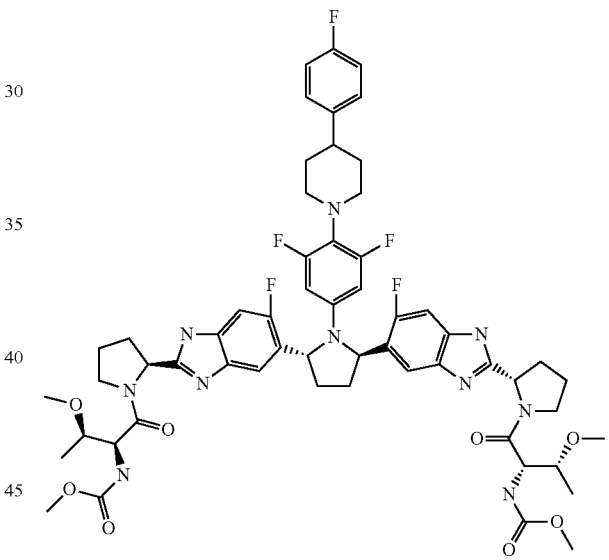

Compound 2 is a potent NS5A inhibitor and is described in U.S. Patent Application Publication No. 2012/0220562.

The current standard of care (SOC) for the treatment of HCV includes a course of treatment of interferon, e.g. pegylated interferon (e.g., pegylated interferon-alpha-2a or pegylated interferon-alpha-2b, such as PEGASYS by Roche, or PEG-INTRON by Schering-Plough) and the antiviral drug ribavirin (e.g., COPEGUS by Roche, REBETOL by Schering-Plough, or RIBASPHERE by Three Rivers Pharmaceuticals). The treatment often lasts for 24-48 weeks, depending on hepatitis C virus genotype. Other interferons include, but are not limited to, interferon-alpha-2a (e.g., Roferon-A by Roche), interferon-alpha-2b (e.g., Intron-A by Schering-Plough), and interferon alfacon-1 (consensus interferon) (e.g., Infergen by Valeant).

The interferon/ribavirin-based treatment may be physically demanding, and can lead to temporary disability in some cases. A substantial proportion of patients will experience a panoply of side effects ranging from a "flu-like" syndrome (the most common, experienced for a few days after the weekly injection of interferon) to severe adverse events including anemia, cardiovascular events and psychiatric problems such as suicide or suicidal ideation. The latter are exacerbated by the general physiological stress experienced by the patients. Ribavirin also has a number of side effects, including, anemia, high pill burden (e.g. 5-6 pills a day split BID) and teratogenicity restricting use in women of childbearing age.

The methods of the present invention provide effective treatment of HCV infection without the use of interferon or ribavirin and for a shorter period of time, for example and without limitation, a treatment duration of no more than twelve weeks, alternatively no more than eleven weeks, alternatively no more than ten weeks, alternatively no more than nine weeks, alternatively no more than eight weeks, alternatively no more than seven weeks, alternatively no more than six weeks, alternatively no more than five weeks, alternatively no more than four weeks, or alternatively, no more than three weeks.

In one aspect, the present invention features methods for treating HCV infection in a subject comprising administering at least two DAAs, in the absence of interferon and ribavirin, to the subject for a duration of no more than twelve weeks, alternatively no more than eight weeks, such as for a duration of 12, 11, 10, 9, 8, 7, 6, 5, or 4 weeks. Put another way, the methods exclude interferon and ribavirin, i.e. neither interferon nor ribavirin are administered. The at least two DAAs comprise Compound 1 (or a pharmaceutically acceptable salt thereof) and Compound 2 (or a pharmaceutically acceptable salt thereof), which can be co-administered, or administered separately or independently, with the same or different dosing frequencies. Preferably, the at least two DAAs are administered once a day. They can also be administered, for example, twice a day or three times a day.

In one aspect, the present invention features methods for treating HCV infection in a subject comprising administering at least two DAAs, in the absence of interferon and ribavirin, to the subject for a duration of no more than twelve weeks, alternatively no more than eight weeks, such as for a duration of 12, 11, 10, 9, 8, 7, 6, 5, or 4 weeks. Put another way, the methods exclude interferon and ribavirin, i.e., neither interferon nor ribavirin are administered. The at least two DAAs comprise Compound 1 (or a pharmaceutically acceptable salt thereof), Compound 2 (or a pharmaceutically acceptable salt thereof) and an HCV polymerase inhibitor, which can be co-administered, or administered separately or independently, with the same or different dosing frequencies. Preferably, the at least two DAAs are administered once a day. They can also be administered, for example, twice a day or three times a day.

In one aspect, the present invention features methods for treating HCV infection in a subject comprising administering at least two DAAs, in the absence of interferon and ribavirin, to the subject for a duration of no more than twelve weeks, alternatively no more than eight weeks, such as for a duration of 12, 11, 10, 9, 8, 7, 6, 5, or 4 weeks. Put another way, the methods exclude interferon and ribavirin, i.e., neither interferon nor ribavirin are administered. The at least two DAAs comprise Compound 1 (or a pharmaceutically acceptable salt thereof), Compound 2 (or a pharmaceutically acceptable salt thereof) and sofosbuvir, which can be co-administered, or administered separately or independently, with the same or different dosing frequencies. Preferably, the at least two DAAs are administered once a day. They can also be administered, for example, twice a day or three times a day.

In one aspect, the present invention features methods for treating HCV infection in a subject comprising administering at least two DAAs, in the absence of interferon and ribavirin, to the subject for a duration of no more than twelve weeks, alternatively no more than eight weeks, such as for a duration of 12, 11, 10, 9, 8, 7, 6, 5, or 4 weeks. Put another way, the methods exclude interferon and ribavirin, i.e., neither interferon nor ribavirin are administered. The at least two DAAs comprise Compound 2 (or a pharmaceutically acceptable salt thereof) and sofosbuvir, which can be co-administered, or administered separately or independently, with the same or different dosing frequencies. Preferably, the at least two DAAs are administered once a day. They can also be administered, for example, twice a day or three times a day.

Various measures may be used to express the effectiveness of a method of the present invention. One such measure is SVR, which, as used herein, means that the virus is undetectable at the end of therapy and for at least 8 weeks after the end of therapy (SVR8); preferably, the virus is undetectable at the end of therapy and for at least 12 weeks after the end of therapy (SVR12); more preferably, the virus is undetectable at the end of therapy and for at least 16 weeks after the end of therapy (SVR16); and highly preferably, the virus is undetectable at the end of therapy and for at least 24 weeks after the end of therapy (SVR24). SVR24 is often considered as a functional definition of cure; and a high rate of SVR at less than 24 week post-treatment (e.g., SVR8 or SVR12) can be predictive of a high rate of SVR24.

Preferably, a method described herein achieves at least 70% SVR8. More preferably, a method described herein achieves at least 80% SVR8. Highly preferably, a method described herein achieves at least 90% SVR8. Most preferably, a method described herein achieves at least 95% SVR8.

Preferably, a method described herein achieves at least 70% SVR12. More preferably, a method described herein achieves at least 80% SVR12. Highly preferably, a method described herein achieves at least 90% SVR12. Most preferably, a method described herein achieves at least 95% SVR12.

In some embodiments, a treatment regimen of the invention comprises treating a population of subjects having HCV infection (e.g. treatment naïve subjects), and the regimen comprises administering at least two DAAs to the subjects for a duration of no more than 12 weeks, or for another duration disclosed herein (e.g., 11, 10, 9, 8, 7, 6, 5, or 4 weeks), wherein the at least two DAAs comprise Compound 1 (or a pharmaceutically acceptable salt thereof) and Compound 2 (or a pharmaceutically acceptable salt thereof), and are administered to the subjects in amounts effective to provide an SVR (e.g., SVR12 or SVR24) in at least about 70% of the population, alternatively at least about 75% of the population, alternatively at least about 80% of the population, alternatively at least about 85% of the population, alternatively at least about 90% of the population, alternatively at least about 95% of the population, alternatively about 100% of the population. In some embodiments, a treatment regimen of the invention comprises treating a population of IFN experienced subjects (e.g., interferon non-responders) having HCV infection, and the method comprises administering at least two DAAs to the subjects for a duration of no more than 12 weeks, or for another duration disclosed herein, wherein the at least two DAAs comprise Compound 1 (or a pharmaceutically acceptable salt thereof) and Compound 2 (or a pharmaceutically acceptable salt thereof), and are administered to the subjects in amounts effective to provide an SVR (e.g., SVR12 or SVR24) in at least about 50% of the population, alternatively at least about 55% of the population, alternatively at least about 60% of the population, alternatively at least about 65% of the population, alternatively at least about 70% of the population, alternatively at least about 75% of the population, alternatively at least about 80% of the population, alternatively at least about 85% of the population, alternatively at least about 90% of the population, alternatively at least about 95% of the population, or alternatively about 100% of the population.

In some embodiments, a treatment regimen of the invention comprises treating a population of subjects having HCV infection (e.g. treatment naïve subjects), and the regimen comprises administering at least two DAAs to the subjects for a duration of no more than 12 weeks, or for another duration disclosed herein (e.g., 11, 10, 9, 8, 7, 6, 5, or 4 weeks), wherein the at least two DAAs comprise Compound 1 (or a pharmaceutically acceptable salt thereof), Compound 2 (or a pharmaceutically acceptable salt thereof) and an HCV polymerase inhibitor, and are administered to the subjects in amounts effective to provide an SVR (e.g., SVR12 or SVR24) in at least about 70% of the population, alternatively at least about 75% of the population, alternatively at least about 80% of the population, alternatively at least about 85% of the population, alternatively at least about 90% of the population, alternatively at least about 95% of the population, alternatively about 100% of the population. In some embodiments, a treatment regimen of the invention comprises treating a population of IFN experienced subjects (e.g., interferon non-responders) having HCV infection, and the method comprises administering at least two DAAs to the subjects for a duration of no more than 12 weeks, or for another duration disclosed herein, wherein the at least two DAAs comprise Compound 1 (or a pharmaceutically acceptable salt thereof), Compound 2 (or a pharmaceutically acceptable salt thereof) and an HCV polymerase inhibitor, and are administered to the subjects in amounts effective to provide an SVR (e.g., SVR12 or SVR24) in at least about 50% of the population, alternatively at least about 55% of the population, alternatively at least about 60% of the population, alternatively at least about 65% of the population, alternatively at least about 70% of the population, alternatively at least about 75% of the population, alternatively at least about 80% of the population, alternatively at least about 85% of the population, alternatively at least about 90% of the population, alternatively at least about 95% of the population, or alternatively about 100% of the population.

In some embodiments, a treatment regimen of the invention comprises treating a population of subjects having HCV infection (e.g. treatment naïve subjects), and the regimen comprises administering at least two DAAs to the subjects for a duration of no more than 12 weeks, or for another duration disclosed herein (e.g., 11, 10, 9, 8, 7, 6, 5, or 4 weeks), wherein the at least two DAAs comprise Compound 1 (or a pharmaceutically acceptable salt thereof), Compound 2 (or a pharmaceutically acceptable salt thereof) and sofosbuvir, and are administered to the subjects in amounts effective to provide an SVR (e.g., SVR12 or SVR24) in at least about 70% of the population, alternatively at least about 75% of the population, alternatively at least about 80% of the population, alternatively at least about 85% of the population, alternatively at least about 90% of the population, alternatively at least about 95% of the population, alternatively about 100% of the population. In some embodiments, a treatment regimen of the invention comprises treating a population of IFN experienced subjects (e.g., interferon non-responders) having HCV infection, and the method comprises administering at least two DAAs to the subjects for a duration of no more than 12 weeks, or for another duration disclosed herein, wherein the at least two DAAs comprise Compound 1 (or a pharmaceutically acceptable salt thereof), Compound 2 (or a pharmaceutically acceptable salt thereof) and sofosbuvir, and are administered to the subjects in amounts effective to provide an SVR (e.g., SVR12 or SVR24) in at least about 50% of the population, alternatively at least about 55% of the population, alternatively at least about 60% of the population, alternatively at least about 65% of the population, alternatively at least about 70% of the population, alternatively at least about 75% of the population, alternatively at least about 80% of the population, alternatively at least about 85% of the population, alternatively at least about 90% of the population, alternatively at least about 95% of the population, or alternatively about 100% of the population.

In some embodiments, a treatment regimen of the invention comprises treating a population of subjects having HCV infection (e.g. treatment naïve subjects), and the regimen comprises administering at least two DAAs to the subjects for a duration of no more than 12 weeks, or for another duration disclosed herein (e.g., 11, 10, 9, 8, 7, 6, 5, or 4 weeks), wherein the at least two DAAs comprise Compound 2 (or a pharmaceutically acceptable salt thereof) and sofosbuvir, and are administered to the subjects in amounts effective to provide an SVR (e.g., SVR12 or SVR24) in at least about 70% of the population, alternatively at least about 75% of the population, alternatively at least about 80% of the population, alternatively at least about 85% of the population, alternatively at least about 90% of the population, alternatively at least about 95% of the population, alternatively about 100% of the population. In some embodiments, a treatment regimen of the invention comprises treating a population of IFN experienced subjects (e.g., interferon non-responders) having HCV infection, and the method comprises administering at least two DAAs to the subjects for a duration of no more than 12 weeks, or for another duration disclosed herein, wherein the at least two DAAs comprise Compound 2 (or a pharmaceutically acceptable salt thereof) and sofosbuvir, and are administered to the subjects in amounts effective to provide an SVR (e.g., SVR12 or SVR24) in at least about 50% of the population, alternatively at least about 55% of the population, alternatively at least about 60% of the population, alternatively at least about 65% of the population, alternatively at least about 70% of the population, alternatively at least about 75% of the population, alternatively at least about 80% of the population, alternatively at least about 85% of the population, alternatively at least about 90% of the population, alternatively at least about 95% of the population, or alternatively about 100% of the population.

It was unexpected that an interferon-free treatment using a combination of Compound 1 (or a pharmaceutically acceptable salt thereof) and Compound 2 (or a pharmaceutically acceptable salt thereof), in the absence of interferon and ribavirin, and for a duration of no more than 12 weeks, can achieve significant SVR.

Accordingly, in one aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 8 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 7 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 6 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 5 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 4 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 3 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 24 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 13 to 23 weeks (e.g., the duration of the treatment is selected from 13, 14, 15, 16, 17, 18, 19, 20, 21, 22 or 23 weeks) and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 12 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

As used in this application, an HCV polymerase inhibitor can be a nucleoside polymerase inhibitor, a nucleotide polymerase inhibitor, a non-nucleoside polymerase inhibitor, or a non-nucleotide polymerase inhibitor.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 11 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 10 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 9 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 8 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 7 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 6 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 5 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 4 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 3 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 24 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 13 to 23 weeks (e.g., the duration of the treatment is selected from 13, 14, 15, 16, 17, 18, 19, 20, 21, 22 or 23 weeks) and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 12 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 11 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 10 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 9 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 8 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 7 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 6 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 5 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 4 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 3 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 24 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 13 to 23 weeks (e.g., the duration of the treatment is selected from 13, 14, 15, 16, 17, 18, 19, 20, 21, 22 or 23 weeks) and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 12 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 11 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 10 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 9 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 8 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 7 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 6 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 5 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 4 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 3 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 24 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 13 to 23 weeks (e.g., the duration of the treatment is selected from 13, 14, 15, 16, 17, 18, 19, 20, 21, 22 or 23 weeks) and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 12 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 11 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 10 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 9 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In each aspect, embodiment, example or method described herein, Compound 1 (or a pharmaceutically acceptable salt thereof) can be administered, for example and without limitation, from 100 mg to 600 mg once daily, and Compound 2 (or a pharmaceutically acceptable salt thereof) can be administered, for example and without limitation, from 50 to 500 mg once daily. More preferably, Compound 1 (or a pharmaceutically acceptable salt thereof) is administered from 200 mg to 600 mg once daily, and Compound 2 (or a pharmaceutically acceptable salt thereof) is administered from 100 to 500 mg once daily. Highly preferably, Compound 1 (or a pharmaceutically acceptable salt thereof) is administered from 400 mg to 600 mg once daily, and Compound 2 (or a pharmaceutically acceptable salt thereof) is administered from 100 to 500 mg once daily. Most preferably, Compound 1 (or a pharmaceutically acceptable salt thereof) is administered from 200 mg to 300 mg once daily, and Compound 2 (or a pharmaceutically acceptable salt thereof) is administered from 100 to 500 mg once daily. Preferably, Compound 1 (or a pharmaceutically acceptable salt thereof) can be administered 200 mg once daily, and Compound 2 (or a pharmaceutically acceptable salt thereof) is administered 120 mg once daily. Also preferably, Compound 1 (or a pharmaceutically acceptable salt thereof) can be administered 300 mg once daily, and Compound 2 (or a pharmaceutically acceptable salt thereof) is administered 120 mg once daily. For another example, Compound 1 (or a pharmaceutically acceptable salt thereof)

can be administered 400 mg once daily, and Compound 2 (or a pharmaceutically acceptable salt thereof) is administered 120 mg once daily. For yet another example, Compound 1 (or a pharmaceutically acceptable salt thereof) can be administered 400 mg once daily, and Compound 2 (or a pharmaceutically acceptable salt thereof) can be administered 240 mg once daily.

In each aspect, embodiment, example or method described herein, sofosbuvir can be administered, for example and without limitation, 400 mg once daily.

A method of the present invention can be used to treat a naïve patient or a treatment experienced patient. Treatment experienced patients include interferon non-responders (e.g., null responders), partial responders, and relapsers. A method of the present invention can also be used to treat patients who are not candidates for interferon treatment. Patients who are not candidates for interferon treatment include, but are not limited to, one or more of the following groups: patients intolerant to interferon, patients who refuse to take interferon treatment, patients with medical conditions which preclude them from taking interferon, and patients who have an increased risk of side effects or infection by taking interferon.

In any method described herein wherein Compound 1 and Compound 2 are used, one or more additional DAAs can be optionally used in the treatment regimen in addition to Compound 1 (or a salt thereof) and Compound 2 (or a salt thereof). Similarly, in any method described herein wherein Compound 1, Compound 2 and sofosbuvir are used, one or more additional DAAs can be optionally used in the treatment regimen in addition to Compound 1 (or a salt thereof), Compound 2 (or a salt thereof) and sofosbuvir. Likewise, in any method described herein wherein Compound 2 and sofosbuvir are used, one or more additional DAAs can be optionally used in the treatment regimen in addition to Compound 2 (or a salt thereof) and sofosbuvir. These additional DAAs can be HCV protease inhibitors, HCV nucleoside or nucleotide polymerase inhibitors, HCV non-nucleoside polymerase inhibitors, HCV NS3B inhibitors, HCV NS4A inhibitors, HCV NS5A inhibitors, HCV NS5B inhibitors, HCV entry inhibitors, cyclophilin inhibitors, or combinations thereof.

Preferred HCV protease inhibitors for this purpose include, but are not limited to, telaprevir (Vertex), boceprevir (Merck), BI-201335 (Boehringer Ingelheim), GS-9451 (Gilead), and BMS-650032 (BMS). Other suitable protease inhibitors include, but are not limited to, ACH-1095 (Achillion), ACH-1625 (Achillion), ACH-2684 (Achillion), AVL-181 (Avila), AVL-192 (Avila), BMS-650032 (BMS), danoprevir (RG7227/ITMN-191, Roche), GS-9132 (Gilead), GS-9256 (Gilead), IDX-136 (Idenix), IDX-316 (Idenix), IDX-320 (Idenix), MK-5172 (Merck), narlaprevir (Schering-Plough Corp), PHX-1766 (Phenomix), TMC-435 (Tibotec), vaniprevir (MK-7009, Merck), VBY708 (Virobay), VX-500 (Vertex), VX-813 (Vertex), VX-985 (Vertex), or a combination thereof.

Preferred non-nucleoside HCV polymerase inhibitors for use in the present invention include, but are not limited to, GS-9190 (Gilead), BI-207127 (Boehringer Ingelheim), and VX-222 (VCH-222) (Vertex & ViraChem). Preferred nucleotide HCV polymerase inhibitors include, but are not limited to, PSI-7977 (Gilead), and PSI-938 (Gilead). Other suitable and non-limiting examples of suitable HCV polymerase inhibitors include ANA-598 (Anadys), BI-207127 (Boehringer Ingelheim), BILB-1941 (Boehringer Ingelheim), BMS-791325 (BMS), filibuvir, GL59728 (Glaxo), GL60667 (Glaxo), GS-9669 (Gilead), IDX-375 (Idenix), MK-3281 (Merck), tegobuvir, TMC-647055 (Tibotec), VCH-759 (Vertex & ViraChem), VCH-916 (ViraChem), VX-759 (Vertex), GS-6620 (Gilead), IDX-102 (Idenix), IDX-184 (Idenix), INX-189 (Inhibitex), MK-0608 (Merck), RG7128 (Roche), TMC64912 (Medivir), GSK625433 (GlaxoSmithKline), BCX-4678 (BioCryst), ALS-2200 (Alios BioPharma/Vertex), ALS-2158 (Alios BioPharma/Vertex), or a combination thereof. A polymerase inhibitor may be a nucleoside or nucleotide polymerase inhibitor, such as GS-6620 (Gilead), IDX-102 (Idenix), IDX-184 (Idenix), INX-189 (Inhibitex), MK-0608 (Merck), PSI-7977 (Gilead), PSI-938 (Gilead), RG7128 (Roche), TMC64912 (Medivir), ALS-2200 (Alios BioPharma/Vertex), ALS-2158 (Alios BioPharma/Vertex), or a combination therefore. A polymerase inhibitor may also be a non-nucleoside polymerase inhibitor, such as PF-00868554 (Pfizer), ANA-598 (Anadys), BI-207127 (Boehringer Ingelheim), BILB-1941 (Boehringer Ingelheim), BMS-791325 (BMS), filibuvir, GL59728 (Glaxo), GL60667 (Glaxo), GS-9669 (Gilead), IDX-375 (Idenix), MK-3281 (Merck), tegobuvir (Gilead), TMC-647055 (Tibotec), VCH-759 (Vertex & ViraChem), VCH-916 (ViraChem), VX-222 (VCH-222) (Vertex & ViraChem), VX-759 (Vertex), or a combination thereof.

Preferred NS5A inhibitors include, but are not limited to, BMS-790052 (BMS) and GS-5885 (Gilead). Non-limiting examples of suitable NS5A inhibitors include GSK62336805 (GlaxoSmithKline), ACH-2928 (Achillion), AZD2836 (Astra-Zeneca), AZD7295 (Astra-Zeneca), BMS-790052 (BMS), BMS-824393 (BMS), GS-5885 (Gilead), PPI-1301 (Presidio), PPI-461 (Presidio) A-831 (Arrow Therapeutics), A-689 (Arrow Therapeutics) or a combination thereof.

Non-limiting examples of suitable cyclophilin inhibitors include alisporovir (Novartis & Debiopharm), NM-811 (Novartis), SCY-635 (Scynexis), or a combination thereof.

Non-limiting examples of suitable HCV entry inhibitors include ITX-4520 (iTherx), ITX-5061 (iTherx), or a combination thereof.

Specific examples of other DAA agents that are suitable for inclusion in a method of the present invention include, but are not limited to, AP-H005, A-831 (Arrow Therapeutics) (NS5A inhibitor), A-689 (Arrow Therapeutics) (NS5A inhibitor), INX08189 (Inhibitex) (polymerase inhibitor), ITMN-191 (Intermune/Roche) (NS3/4A Protease inhibitor), VBY-376 (Protease Inhibitor) (Virobay), ACH-1625 (Achillion, Protease inhibitor), IDX136 (Idenix, Protease Inhibitor), IDX316 (Idenix, Protease inhibitor), VX-813 (Vertex), SCH 900518 (Schering-Plough), TMC-435 (Tibotec), ITMN-191 (Intermune, Roche), MK-7009 (Merck), IDX-PI (Novartis), R7128 (Roche), PF-868554 (Pfizer) (non-nucleoside polymerase inhibitor), PF-4878691 (Pfizer), IDX-184 (Idenix), IDX-375 (Idenix, NS5B polymerase inhibitor), PPI-461 (Presidio), BILB-1941 (Boehringer Ingelheim), GS-9190 (Gilead), BMS-790052 (BMS), CTS-1027 (Conatus), GS-9620 (Gilead), PF-4878691 (Pfizer), R05303253 (Roche), ALS-2200 (Alios BioPharma/Vertex), ALS-2158 (Alios BioPharma/Vertex), GSK62336805 (GlaxoSmithKline), or any combinations thereof.

The chemical structures of some of these optional HCV inhibitors are provided below:

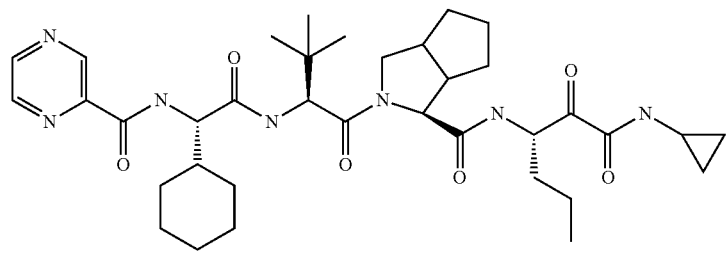
Telaprevir
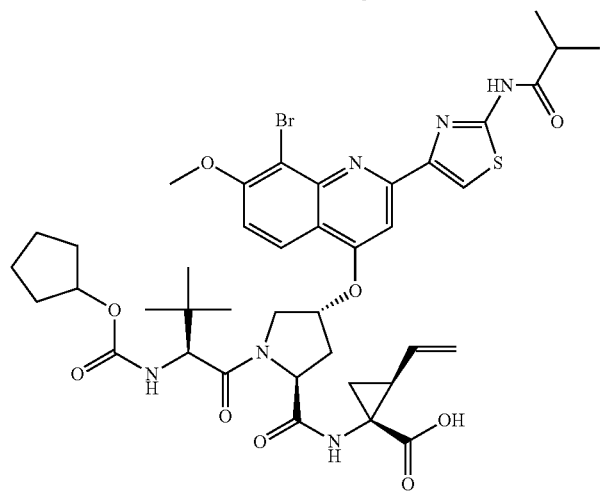
BI-201335
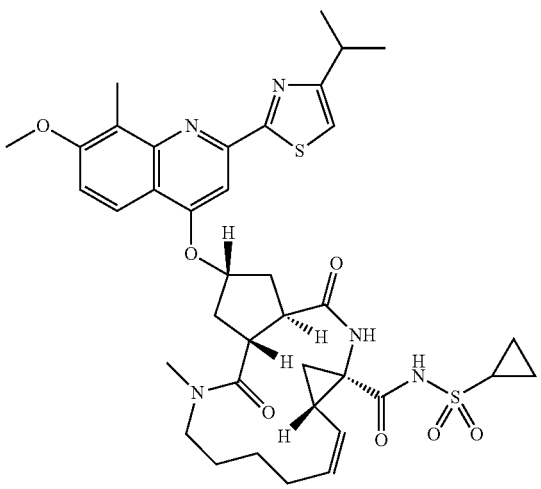
TMC-435 (TMC-435350)
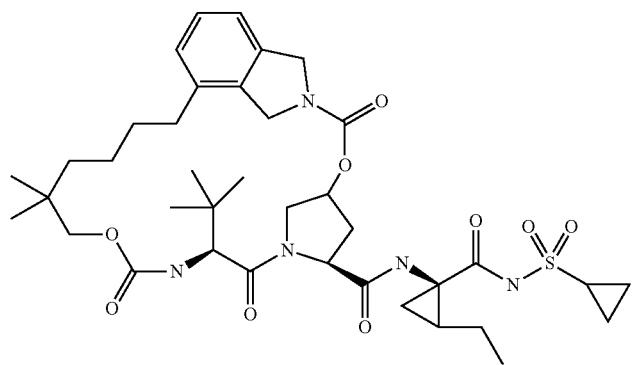
Vaniprevir, MK-7009
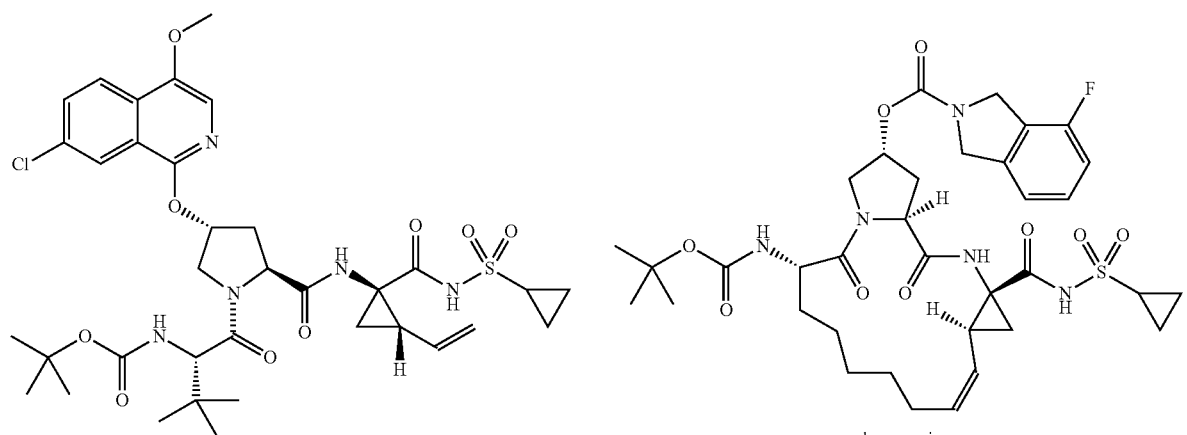
BMS-650032 (Asunaprevir)
danoprevir

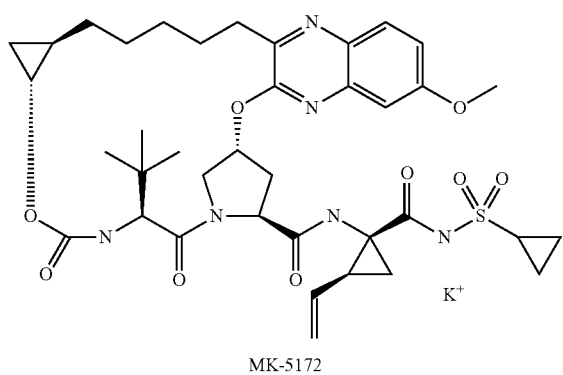
MK-5172
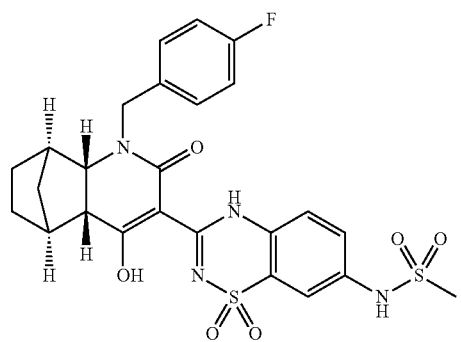
ANA-598 (Setrobuvir)
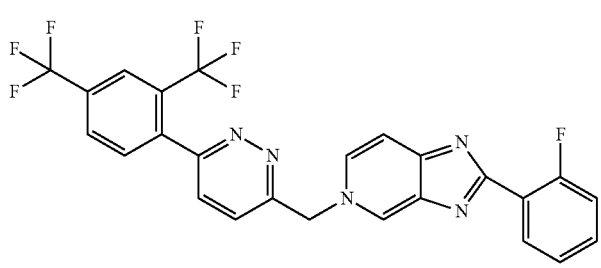
GS-333126 (GS-9190 or tegobuvir)
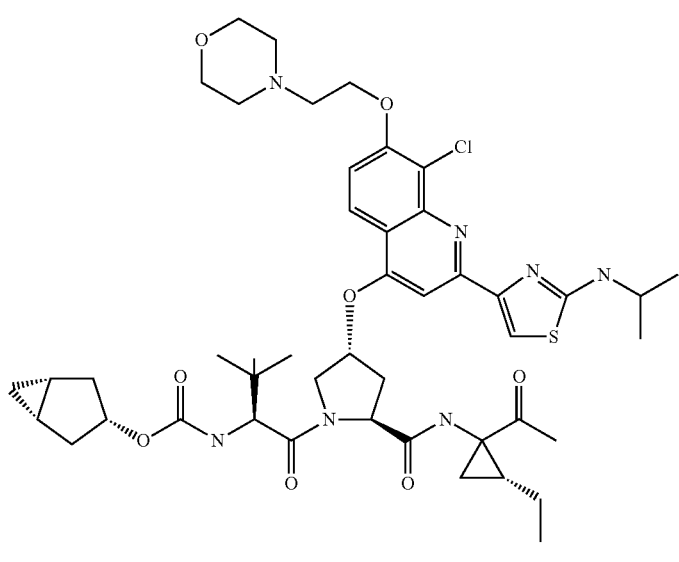
GS-9451
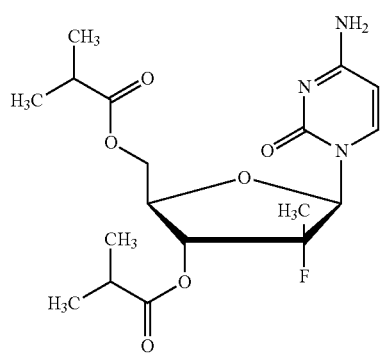
Mericitabine (R-4048 or RG7128)
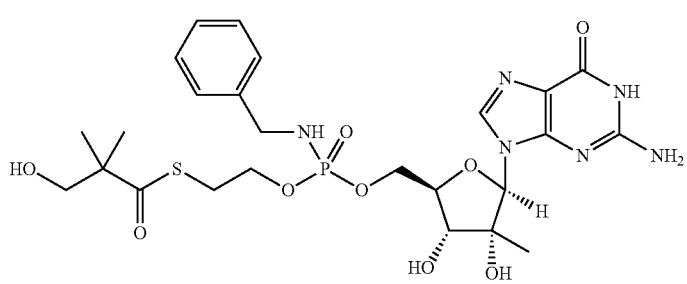
IDX-184

-continued
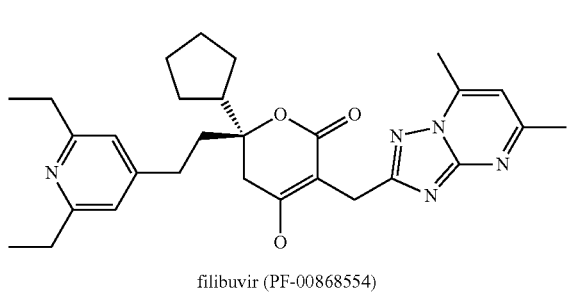
filibuvir (PF-00868554)
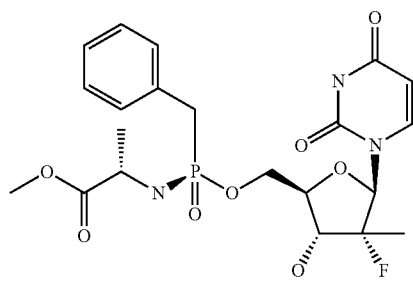
PSI-7977
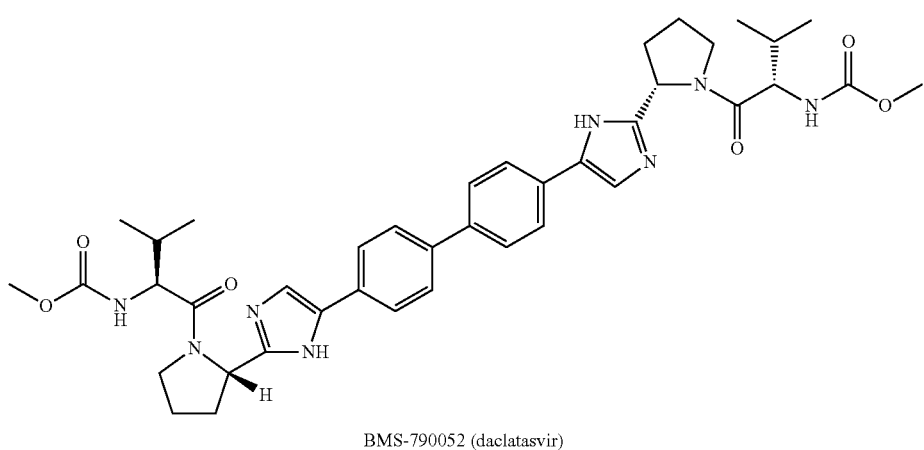
BMS-790052 (daclatasvir)
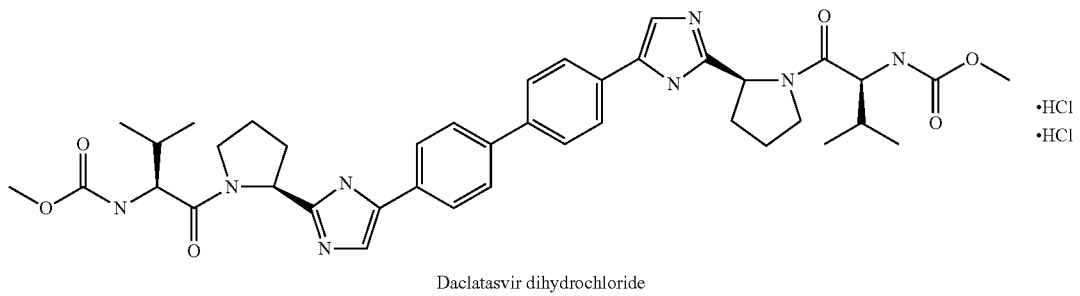
Daclatasvir dihydrochloride
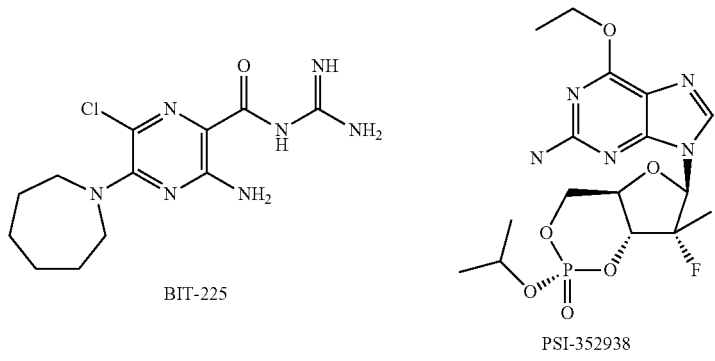
BIT-225
PSI-352938

-continued

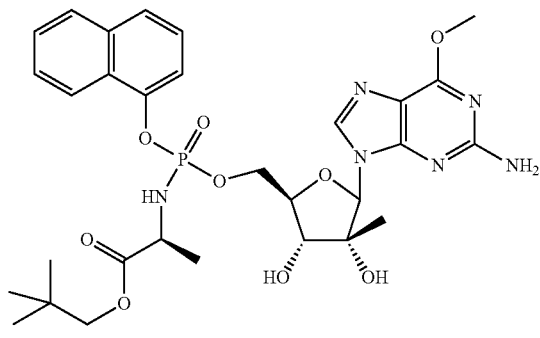
INX-189

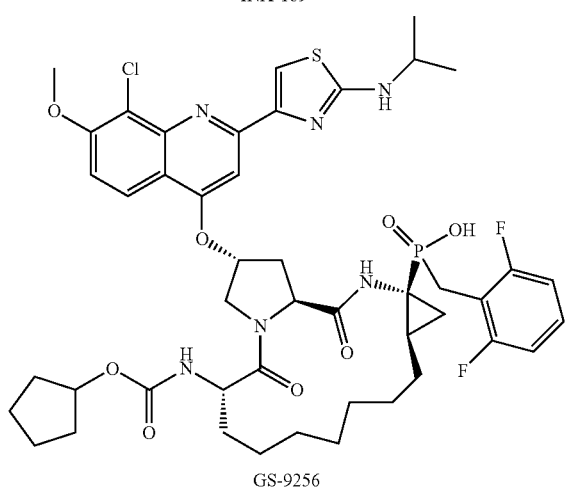
GS-9256

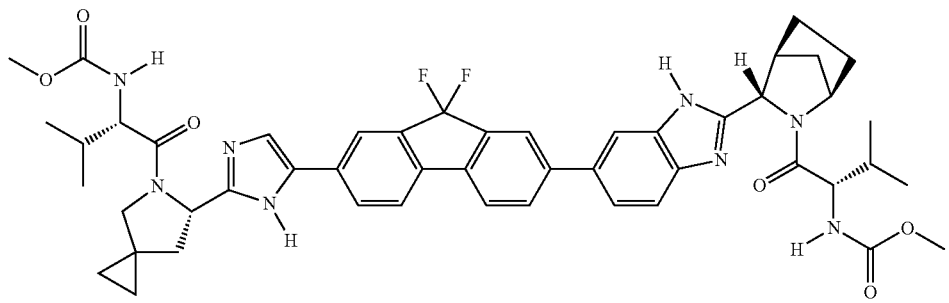
GS-5885

Any HCV inhibitor or DAA described herein encompasses its suitable salt forms when it is used in therapeutic treatments or pharmaceutical formulations.

In some embodiments, the present invention features methods for treating patients infected with HCV genotype 1, such as 1a or 1b. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof) and Compound 2 (a pharmaceutically acceptable salt thereof). Compound 1 (or a pharmaceutically acceptable salt thereof) and Compound 2 (a pharmaceutically acceptable salt thereof) can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 2 or 3 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof) and Compound 2 (a pharmaceutically acceptable salt thereof). Compound 1 (or a pharmaceutically acceptable salt thereof) and Compound 2 (a pharmaceutically acceptable salt thereof) can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 2 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof) and Compound 2 (a pharmaceutically acceptable salt thereof). Compound 1 (or a pharmaceutically acceptable salt thereof) and Compound 2 (a pharmaceutically acceptable salt thereof) can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 3 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof) and Compound 2 (a pharmaceutically acceptable salt thereof). Compound 1 (or a pharmaceutically acceptable salt thereof) and Compound 2 (a pharmaceutically acceptable salt thereof) can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 4 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof) and Compound 2 (a pharmaceutically acceptable salt thereof). Compound 1 (or a pharmaceutically acceptable salt thereof) and Compound 2 (a pharmaceutically acceptable salt thereof) can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 5 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof) and Compound 2 (a pharmaceutically acceptable salt thereof). Compound 1 (or a pharmaceutically acceptable salt thereof) and Compound 2 (a pharmaceutically acceptable salt thereof) can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 6 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof) and Compound 2 (a pharmaceutically acceptable salt thereof). Compound 1 (or a pharmaceutically acceptable salt thereof) and Compound 2 (a pharmaceutically acceptable salt thereof) can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients infected with HCV genotype 1, such as 1a or 1b. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin (i.e., neither interferon nor ribavirin are administered), and said at least 2 DAAs comprise Compound 1 (or a pharmaceutically acceptable salt thereof), Compound 2 (a pharmaceutically acceptable salt thereof) and an HCV polymerase inhibitor. Compound 1 (or a pharmaceutically acceptable salt thereof), Compound 2 (a pharmaceutically acceptable salt thereof) and the HCV polymerase inhibitor can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 2 or 3 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and an HCV polymerase inhibitor. Compound 1 (or a pharmaceutically acceptable salt thereof), Compound 2 (a pharmaceutically acceptable salt thereof) and the HCV polymerase inhibitor can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 2 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and an HCV polymerase inhibitor. Compound 1 (or a pharmaceutically acceptable salt thereof), Compound 2 (a pharmaceutically acceptable salt thereof) and the HCV polymerase inhibitor can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 3 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and an HCV polymerase inhibitor. Compound 1 (or a pharmaceutically acceptable salt thereof), Compound 2 (a pharmaceutically acceptable salt thereof) and the HCV polymerase inhibitor can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 4 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and an HCV polymerase inhibitor. Compound 1 (or a pharmaceutically acceptable salt thereof), Compound 2 (a pharmaceutically acceptable salt thereof) and the HCV polymerase inhibitor can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 5 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and an HCV polymerase inhibitor. Compound 1 (or a pharmaceutically acceptable salt thereof), Compound 2 (a pharmaceutically acceptable salt thereof) and the HCV polymerase inhibitor can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 6 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and an HCV polymerase inhibitor. Compound 1 (or a pharmaceutically acceptable salt thereof), Compound 2 (a pharmaceutically acceptable salt thereof) and the HCV polymerase inhibitor can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients infected with HCV genotype 1, such as 1a or 1b. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and sofosbuvir. Compound 1 (or a pharmaceutically acceptable salt thereof), Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 2 or 3 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and sofosbuvir. Compound 1 (or a pharmaceutically acceptable salt thereof), Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 2 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and sofosbuvir. Compound 1 (or a pharmaceutically acceptable salt thereof), Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 3 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and sofosbuvir. Compound 1 (or a pharmaceutically acceptable salt thereof), Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 4 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and sofosbuvir. Compound 1 (or a pharmaceutically acceptable salt thereof), Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 5 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and sofosbuvir. Compound 1 (or a pharmaceutically acceptable salt thereof), Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 6 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and sofosbuvir. Compound 1 (or a pharmaceutically acceptable salt thereof), Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients infected with HCV genotype 1, such as 1a or 1b. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 2 (a pharmaceutically acceptable salt thereof) and sofosbuvir. Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 2 or 3 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 2 (a pharmaceutically acceptable salt thereof) and sofosbuvir. Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 2 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 2 (a pharmaceutically acceptable salt thereof) and sofosbuvir. Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 3 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 2 (a pharmaceutically acceptable salt thereof) and sofosbuvir. Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 4 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 2 (a pharmaceutically acceptable salt thereof) and sofosbuvir. Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 5 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 2 (a pharmaceutically acceptable salt thereof) and sofosbuvir. Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 6 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 2 (a pharmaceutically acceptable salt thereof) and sofosbuvir. Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

It will be understood that the specific dose level for any particular patient will depend upon a variety of factors including the activity of the specific compound employed, the age, body weight, general health, sex, diet, time of administration, route of administration, rate of excretion, drug combination, and the severity of the disease undergoing therapy.

In any method described herein wherein Compound 1 and Compound 2 are used, Compound 1 (or a pharmaceutically acceptable salt thereof) and Compound 2 (a pharmaceutically acceptable salt thereof) may be co-formulated in a single dosage form. Non-limiting examples of suitable dosage forms include liquid or solid dosage forms. Preferably, Compound 1 and Compound 2 are formulated in a single solid dosage form in which at least one of the DAAs is in an amorphous form, or highly preferably molecularly dispersed, in a matrix which comprises a pharmaceutically acceptable water-soluble polymer and a pharmaceutically acceptable surfactant. The other DAAs can also be in an amorphous form or molecularly dispersed in the matrix, or formulated in different form(s) (e.g., in a crystalline form). More preferably, each of the two DAAs is in an amorphous form, or highly preferably molecularly dispersed, in a matrix which comprises a pharmaceutically acceptable water-soluble polymer and a pharmaceutically acceptable surfactant.

In any method described herein wherein Compound 1, Compound 2 and sofosbuvir are used, Compound 1 (or a pharmaceutically acceptable salt thereof), Compound 2 (a pharmaceutically acceptable salt thereof) and sofosbuvir may be co-formulated in a single dosage form. Non-limiting examples of suitable dosage forms include liquid or solid dosage forms. Preferably, Compound 1, Compound 2 and sofosbuvir are formulated in a single solid dosage form in which at least one of the DAAs is in an amorphous form, or highly preferably molecularly dispersed, in a matrix which comprises a pharmaceutically acceptable water-soluble polymer and a pharmaceutically acceptable surfactant. The other DAAs can also be in an amorphous form or molecularly dispersed in the matrix, or formulated in different form(s) (e.g., in a crystalline form).

In any method described herein wherein Compound 2 and sofosbuvir are used, Compound 2 (or a pharmaceutically acceptable salt thereof) and sofosbuvir may be co-formulated in a single dosage form. Non-limiting examples of suitable dosage forms include liquid or solid dosage forms. Preferably, Compound 2 and sofosbuvir are formulated in a single solid dosage form in which at least one of the DAAs is in an amorphous form, or highly preferably molecularly dispersed, in a matrix which comprises a pharmaceutically acceptable water-soluble polymer and a pharmaceutically acceptable surfactant. The other DAAs can also be in an amorphous form or molecularly dispersed in the matrix, or formulated in different form(s) (e.g., in a crystalline form).

In any method described herein, the patient being treated can be a treatment-naïve patient.

In any method described herein, the patient being treated can be an interferon non-responder.

In any method described herein, the patient being treated can be an interferon null-responder.

In any method described herein, the patient being treated can be without cirrhosis.

In any method described herein, the patient being treated can be a cirrhotic patient.

In any method described herein, the patient being treated can be a patient with compensated cirrhosis.

It is also contemplated a method of treating HCV, said method comprising administering to a patient in need thereof an effective amount of a combination of two or more DAAs. The treatment lasts 4 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 is (2R,6S,13aS,14aR,16aS,Z)—N-(cyclopropylsulfonyl)-6-(5-methylpyrazine-2-carbox-amido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide, and Compound 4 is as dimethyl (2S,2'S)-1,1'-((2S,2'S)-2,2'-(4,4'-((2S,5S)-1-(4-tert-butylphenyl)pyrrolidine-2,5-diyl)bis(4,1-phenylene))bis(azanediyl)bis(oxomethylene)bis(pyrrolidine-2,1-diyl)bis(3-methyl-1-oxobutane-2,1-diyl)dicarbamate, both of which are described in U.S. Patent Application Publication No. 2013/0102526, filed Oct. 19, 2012 and entitled "Methods for Treating HCV", which is incorporated herein by reference in its entirety. Compound 3 preferably is co-administered with ritonavir. More preferably, Compound 3 is co-formulated with ritonavir. It is believed that the combination of Compound 3, Compound 4, and sofosbuvir, without ribavirin and interferon, can achieve at least about 80% SVR rate against HCV genotype 1 after 4-week treatment. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

It is further contemplated a method of treating HCV, said method comprising administering to a patient in need thereof an effective amount of a combination of two or more DAAs. The treatment lasts 5 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 preferably is co-administered with ritonavir. More preferably, Compound 3 is co-formulated with ritonavir. It is believed that the combination of Compound 3, Compound 4, and sofosbuvir, without ribavirin and interferon, can achieve at least about 80% SVR rate against HCV genotype 1 after 5-week treatment. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

It is further contemplated a method of treating HCV, said method comprising administering to a patient in need thereof an effective amount of a combination of two or more DAAs. The treatment lasts 6 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 preferably is co-administered with ritonavir. More preferably, Compound 3 is co-formulated with ritonavir. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1.

In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily.

In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

It is further contemplated a method of treating HCV, said method comprising administering to a patient in need thereof an effective amount of a combination of two or more DAAs. The treatment lasts 7 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 preferably is co-administered with ritonavir. More preferably, Compound 3 is co-formulated with ritonavir. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

It is further contemplated a method of treating HCV, said method comprising administering to a patient in need thereof an effective amount of a combination of two or more DAAs. The treatment lasts 8 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 preferably is co-administered with ritonavir. More preferably, Compound 3 is co-formulated with ritonavir. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

It is further contemplated a method of treating HCV, said method comprising administering to a patient in need thereof an effective amount of a combination of two or more DAAs. The treatment lasts 9 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 preferably is co-administered with ritonavir. More preferably, Compound 3 is co-formulated with ritonavir. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

It is further contemplated a method of treating HCV, said method comprising administering to a patient in need thereof an effective amount of a combination of two or more DAAs. The treatment lasts 10 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions.

Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 preferably is co-administered with ritonavir. More preferably, Compound 3 is co-formulated with ritonavir. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

It is further contemplated a method of treating HCV, said method comprising administering to a patient in need thereof an effective amount of a combination of two or more DAAs. The treatment lasts 11 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 preferably is co-administered with ritonavir. More preferably, Compound 3 is co-formulated with ritonavir. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

It is further contemplated a method of treating HCV, said method comprising administering to a patient in need thereof an effective amount of a combination of two or more DAAs. The treatment lasts 12 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 preferably is co-administered with ritonavir. More preferably, Compound 3 is co-formulated with ritonavir. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naive patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

In any method described herein, the HCV polymerase inhibitor recited therein can be IDX21437 (a uridine nucleotide analog HCV NS5B polymerase inhibitor, Idenix).

In any method described herein, the HCV polymerase inhibitor recited therein can also be IDX21459.

In any method described herein, the HCV NS5A inhibitor recited therein can be GS-5816.

In any method described herein, the HCV NS5A inhibitor recited therein can also be MK-8742.

In any method described herein, the patient being treated preferably is HCV genotype 1 patient.

It should be understood that the above-described embodiments and the following examples are given by way of illustration, not limitation. Various changes and modifications within the scope of the present invention will become apparent to those skilled in the art from the present description.

Example 1. Clinical Modeling for Interferon-Free DAA Combination Therapies

Treatment regimens comprising administration of Compound 1 and Compound 2 were evaluated using clinical models described in U.S. Patent Application Publication No. 2013/0102526, filed Oct. 19, 2012 and entitled "Methods for Treating HCV", which is incorporated herein by reference in its entirety. These treatment regimens comprised administration of Compound 1 and Compound 2, but did not include administration of either interferon or ribavirin. Comparable SVR rates are expected for interferon-non responders.

FIG. 1 shows the predicted median SVR percentages and 90% SVR confidence intervals for 2-DAA regimens consisting of the use of Compound 1 (400 mg once daily) and Compound 2 (120 mg once daily) to treat genotype 1 naïve subjects. Different treatment durations were assessed. The predicted SVR rate for a 12-week treatment was about 95%. As used in all of the figures of the present application, the vertical bar at the top of each SVR percentage column represents the 90% SVR confidence interval, and the x-axis ("Time (weeks)") indicates the duration of each treatment regimen.

Figure 2:
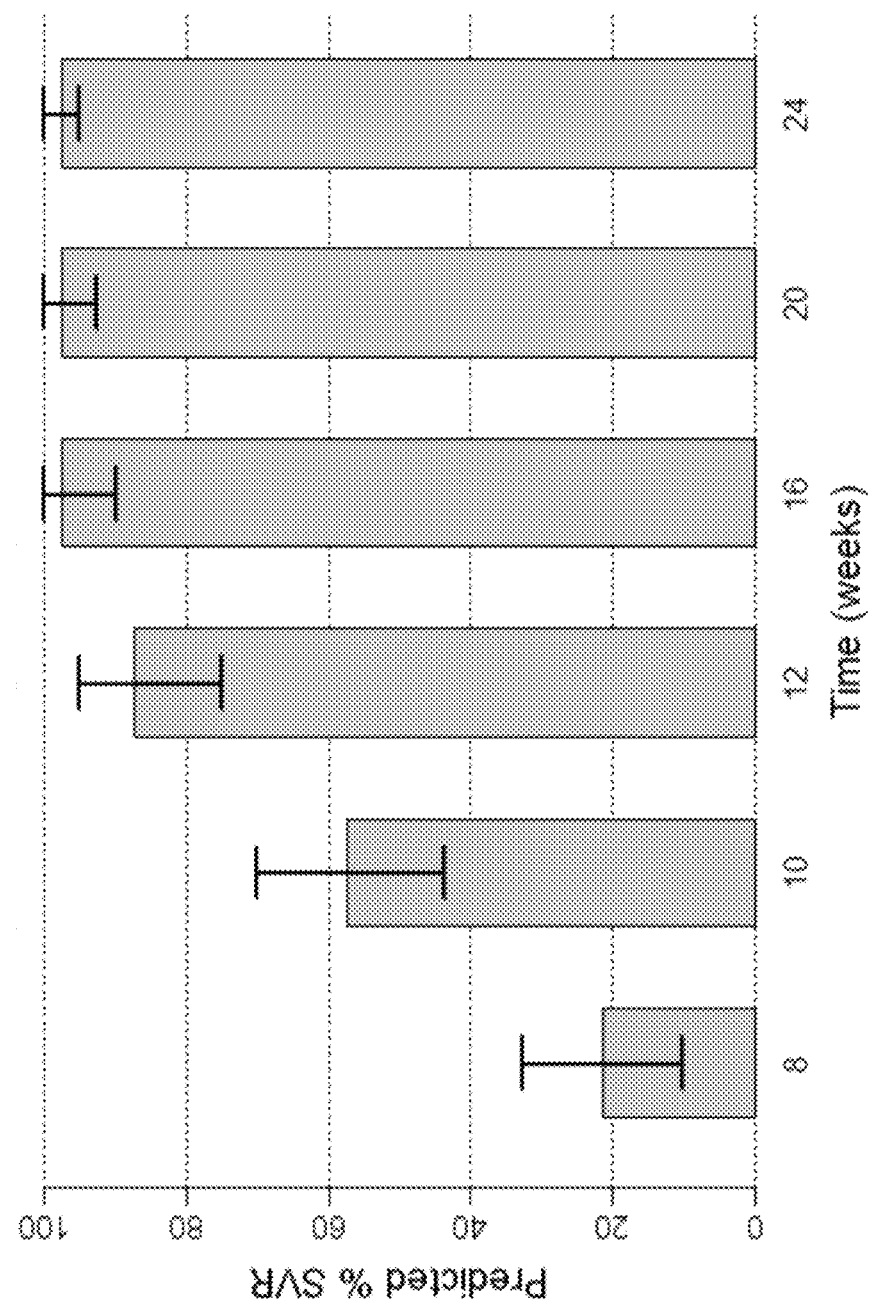
FIG. 2 illustrates the predicted median SVR percentages and 90% SVR confidence intervals for interferon/ribavirin-free, 2-DAA regimens comprising the use of Compound 1 (400 mg once daily) and Compound 2 (60 mg once daily) to treat genotype 1 naïve subjects.

FIG. 2 illustrates the predicted median SVR percentages and 90% SVR confidence intervals for 2-DAA regimens consisting of the use of Compound 1 (400 mg once daily) and Compound 2 (60 mg once daily) to treat genotype 1 naïve subjects. Different treatment durations were assessed. The predicted SVR rate for a 12-week treatment was about 85-90%.

Figure 3:
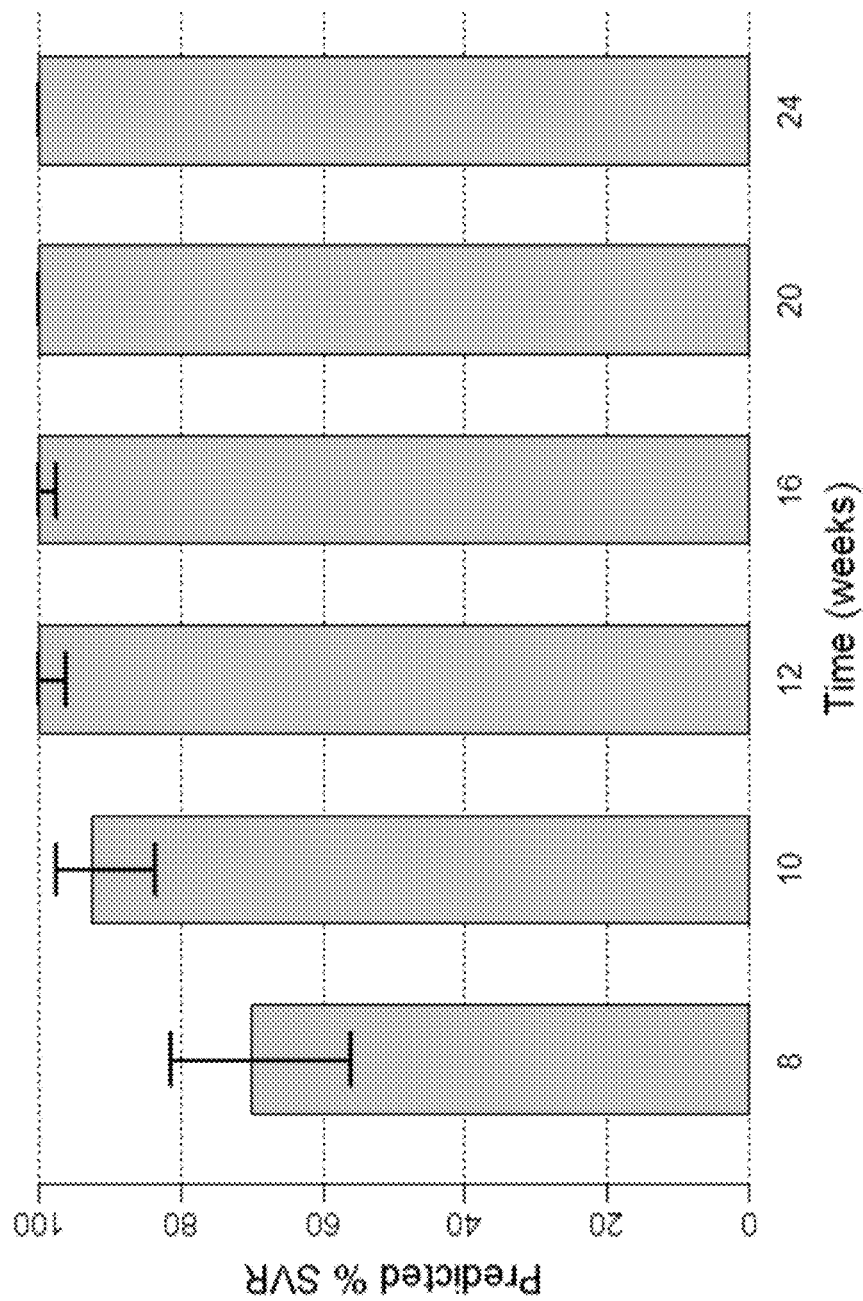
FIG. 3 depicts the predicted median SVR percentages and 90% SVR confidence intervals for interferon/ribavirin-free, 2-DAA regimens comprising the use of Compound 1 (600 mg once daily) and Compound 2 (480 mg once daily) to treat genotype 1 naïve subjects.

FIG. 3 shows the predicted median SVR percentages and 90% SVR confidence intervals for 2-DAA regimens consisting of the use of Compound 1 (600 mg once daily) and Compound 2 (480 mg once daily) to treat genotype 1 naïve subjects. Different treatment durations were assessed. The predicted SVR rate for a 12-week treatment was about 100%.

Figure 4:
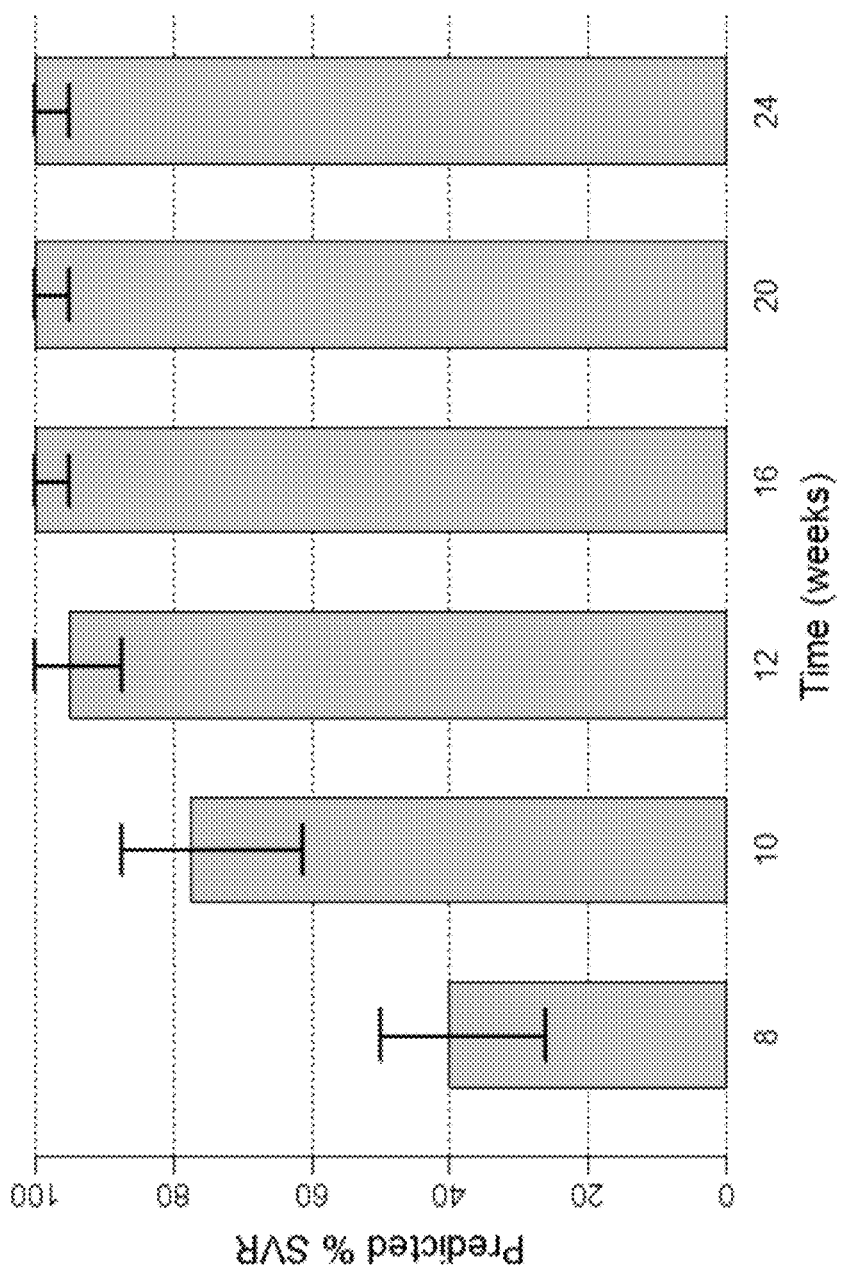
FIG. 4 shows the predicted median SVR percentages and 90% SVR confidence intervals for interferon/ribavirin-free, 2-DAA regimens comprising the use of Compound 1 (400 mg once daily) and Compound 2 (120 mg once daily) to treat genotype 3 naïve subjects.

FIG. 4 depicts the predicted median SVR percentages and 90% SVR confidence intervals for 2-DAA regimen consisting of the use of Compound 1 (400 mg once daily) and Compound 2 (120 mg once daily) to treat genotype 3 naïve subjects. Different treatment durations were assessed. The predicted SVR rate for a 12-week treatment was about 95%.

Figure 5:
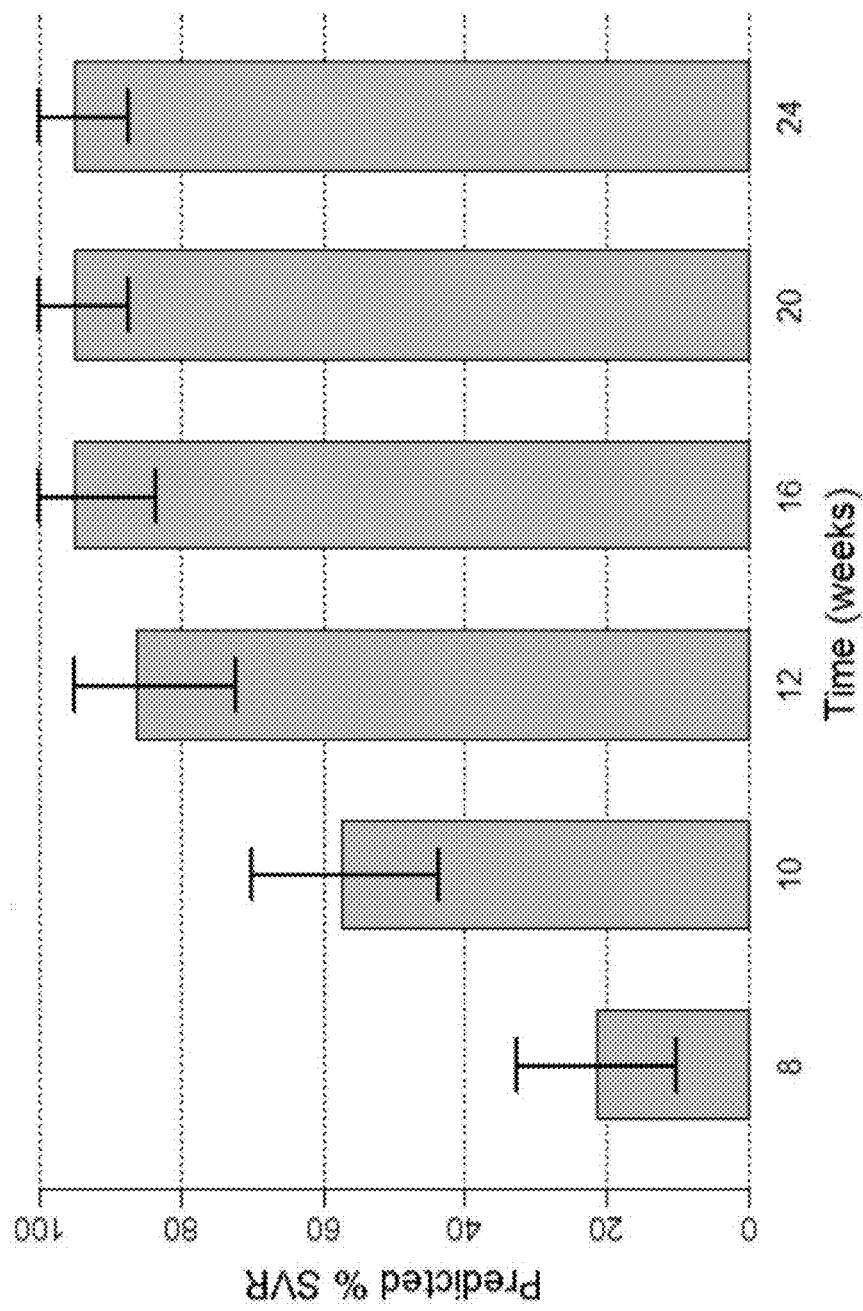
FIG. 5 illustrates the predicted median SVR percentages and 90% SVR confidence intervals for interferon/ribavirin-free, 2-DAA regimens comprising the use of Compound 1 (400 mg once daily) and Compound 2 (60 mg once daily) to treat genotype 3 naïve subjects.

FIG. 5 illustrates the predicted median SVR percentages and 90% SVR confidence intervals for 2-DAA regimen consisting of the use of Compound 1 (400 mg once daily) and Compound 2 (60 mg once daily) to treat genotype 3 naïve subjects. Different treatment durations were assessed. The predicted SVR rate of a 12-week treatment was about 85-90%.

Figure 6:
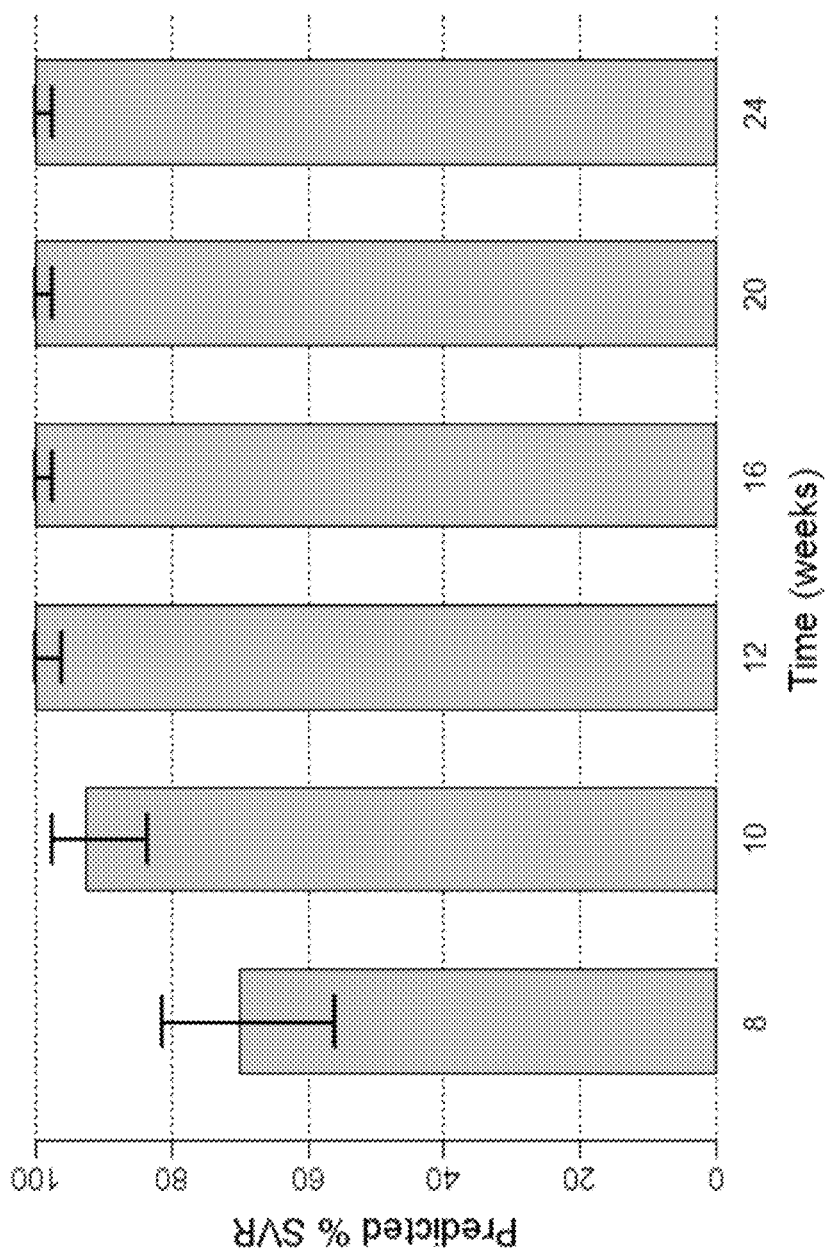
FIG. 6 shows the predicted median SVR percentages and 90% SVR confidence intervals for interferon/ribavirin-free, 2-DAA regimens comprising the use of Compound 1 (600 mg once daily) and Compound 2 (480 mg once daily) to treat genotype 3 naïve subjects.

FIG. 6 shows the predicted median SVR percentages and 90% SVR confidence intervals for 2-DAA regimens consisting of the use of Compound 1 (600 mg once daily) and Compound 2 (480 mg once daily) to treat genotype 3 naïve subjects. Different treatment durations were assessed. The predicted SVR rate of a 12-week treatment was about 100%.

Figure 7:
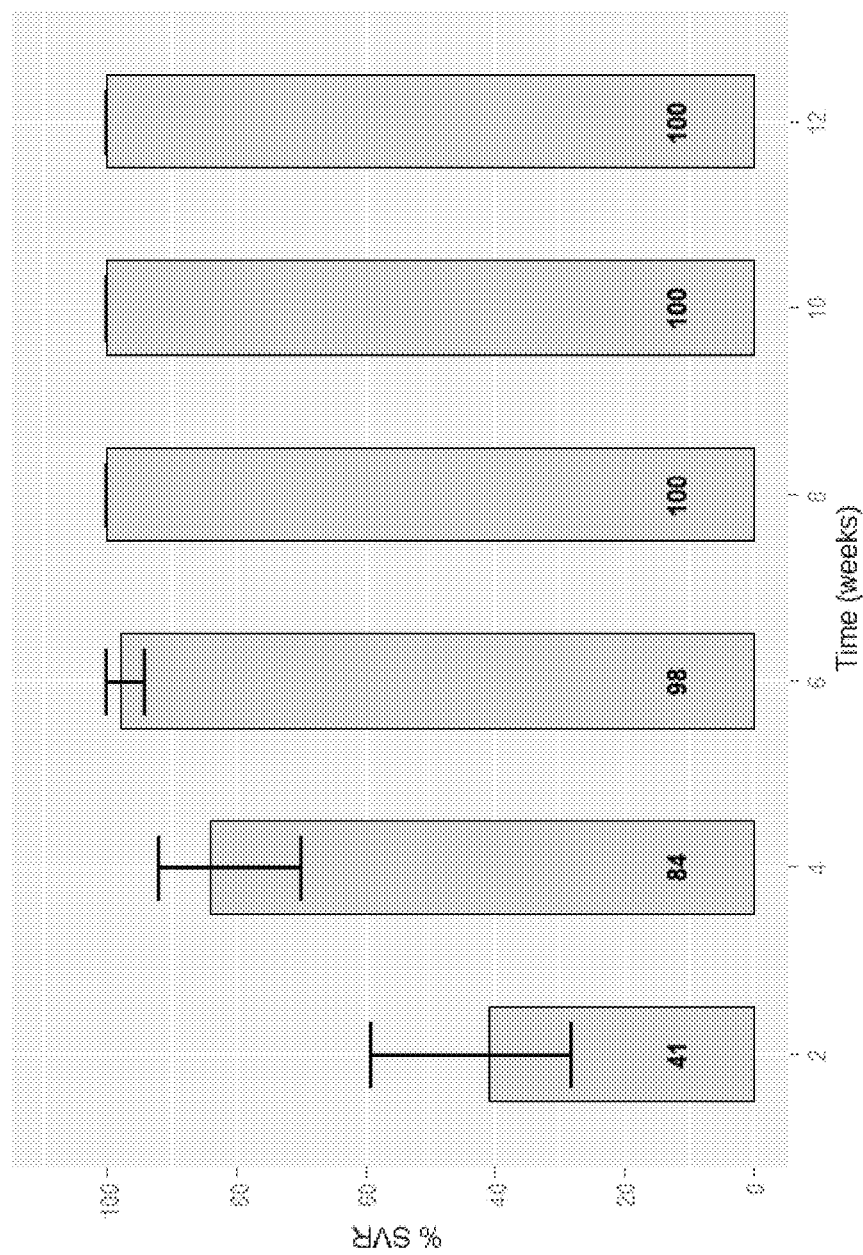
FIG. 7 shows the predicted median SVR percentages and 90% SVR confidence intervals for interferon/ribavirin-free, 3-DAA regimens comprising the use of Compound 1 (400 mg once daily), Compound 2 (120 mg once daily) and sofosbuvir (400 mg once daily) to treat genotype 1 naïve subjects.

Treatment regimens comprising administration of Compound 1, Compound 2 and sofosbuvir, or Compound 2 and sofosbuvir, were also evaluated using the same clinical model. FIG. 7 shows the predicted SVR for the treatment regimen consisting of the use of Compound 1 (400 mg once daily), Compound 2 (120 mg once daily) and sofosbuvir (400 mg once daily) to treat genotype 1 naïve subjects. The treatment regimen did not include administration of either interferon or ribavirin. Different treatment durations were assessed. The predicted SVR rates of the 2-week, 4-week, 6-week, 8-week, 10-week, and 12-week treatment regimens were about 40%, 85%, 100%, 100%, 100%, and 100%, respectively. Comparable SVR rates are expected for interferon-non responders.

Figure 8:
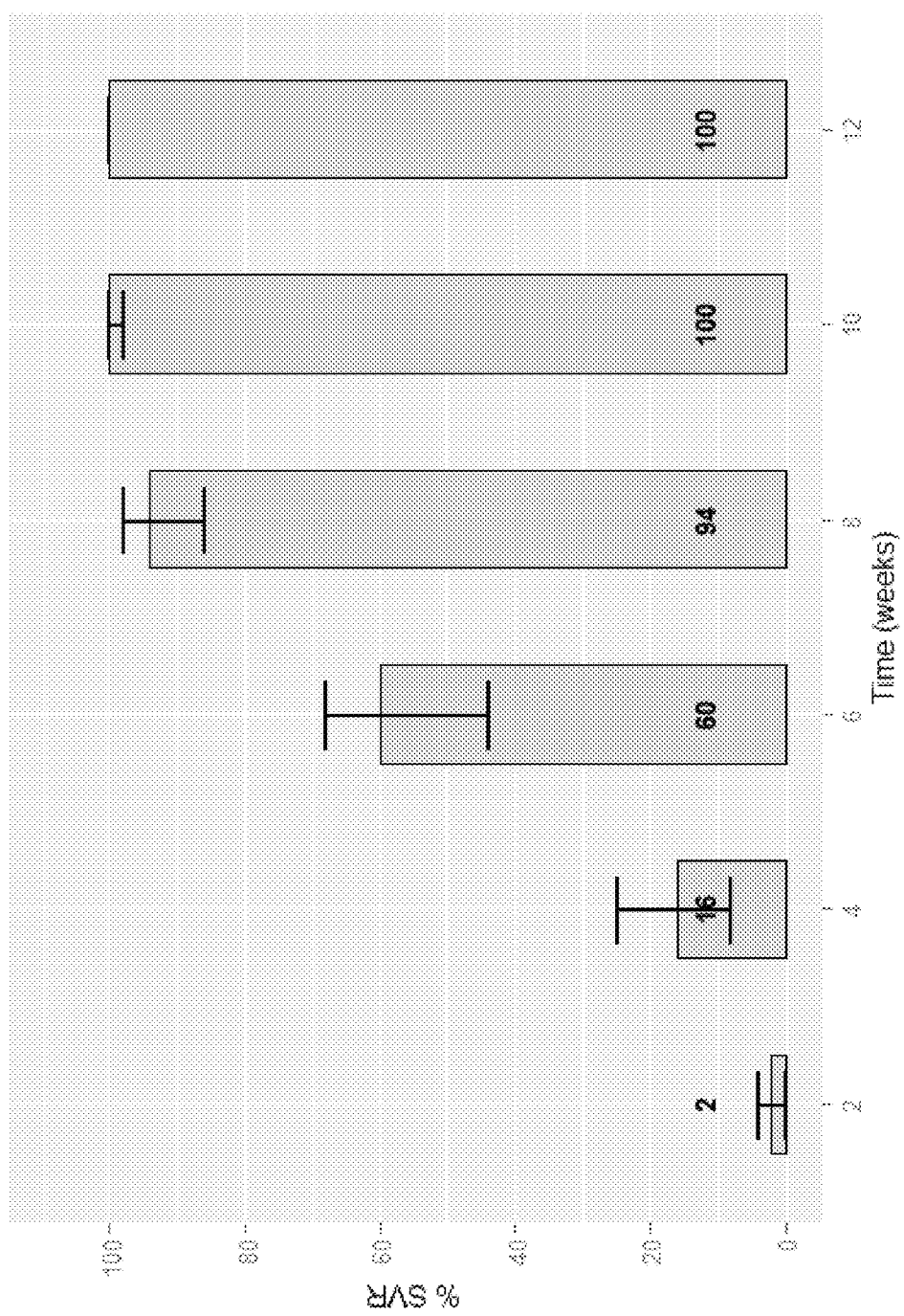
FIG. 8 shows the predicted median SVR percentages and 90% SVR confidence intervals for interferon/ribavirin-free, 2-DAA regimens comprising the use of Compound 2 (120 mg once daily) and sofosbuvir (400 mg once daily) to treat genotype 1 naïve subjects.

FIG. 8 shows the predicted SVR for the treatment regimen consisting of the use of Compound 2 (120 mg once daily) and sofosbuvir (400 mg once daily) to treat genotype 1 naïve subjects. The treatment regimen did not include administration of either interferon or ribavirin. Different treatment durations were assessed. The predicted SVR rates of the 6-week, 8-week, 10-week, and 12-week treatment regimens were about 60%, 95%, 100%, and 100%, respectively. Comparable SVR rates are expected for interferon-non responders.

Example 2. Combination of Compound 1 and Compound 2 In Vitro

Figure 9:
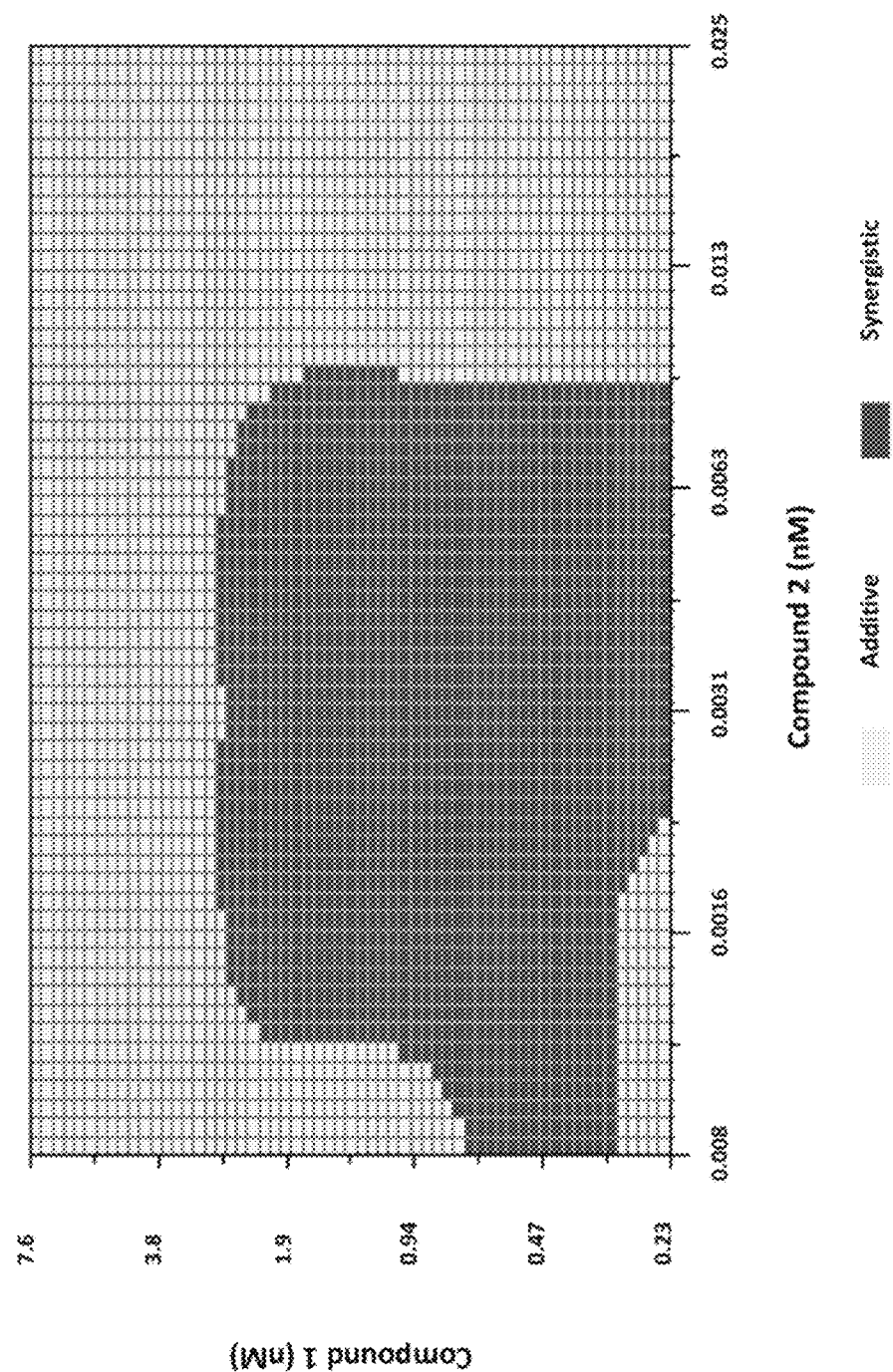
FIG. 9 depict the synergistic effect of the combination of Compound 1 and Compound 2 on HCV inhibition in vitro.

FIG. 9 shows that the combination of Compound 1 and Compound 2 exhibits significant synergistic effect on HCV inhibition as tested in HCV GT 1b Con-1 replication cells. The result was generated using Prichard and Shipman model (Prichard et al. ANTIVIRAL RESEARCH 14:181-205 (1990)).

Compound 1 inhibited replication of HCV stable subgenomic replicons containing NS3 genes from GT 1a, 1b, 2a, 3a, 4a, or 6a with $EC_{50}$ values ranging from 0.85 to 2.8 nM. Of note, Compound 1 was potent against replicon containing GT3a protease, with an $EC_{50}$ value of 1.6 nM. Compound 1 retained its activity against common GT1a and 1b variants at NS3 amino acid positions 155 and 168 that conferred resistance to other HCV protease inhibitors (PIs). Resistant colony selection studies in GT1a and 1b subgenomic replicon cells identified A156T in GT1a and A156V in GT1b as the most frequent variants, which conferred 1400- and 1800-fold reduced susceptibility to Compound 1, respectively. However, these variants had in vitro replication capacities of only 1.5% and 9.2% that of their corresponding wild-type replicons. In a replicon containing GT3a NS3 protease, Compound 1 selected very few colonies at concentrations ≥100-fold over its EC50 value. The colonies that survived the selection contained either A156G alone, or Q168R co-selected with Y56H, which conferred 1500- or 1100-fold loss in susceptibility to Compound 1, respectively.

TABLE 2

Antiviral Activity of Compound 1 in the HCV Subgenomic Stable Replicon Cell Culture Assay

| HCV Replicon Subtype | N[b] | 0% Human Plasma[a] Mean EC$_{50}$, nM, ± Std. Dev. |
|---|---|---|
| Genotype 1a | 9 | 0.85 ± 0.15 |
| Genotype 1b | 8 | 0.94 ± 0.35 |
| Genotype 2a | 2 | 2.7 ± 1.1 |
| Genotype 3a | 2 | 1.6 ± 0.49 |
| Genotype 4a | 4 | 2.8 ± 0.41 |
| Genotype 6a | 4 | 0.86 ± 0.11 |

[a]The 0% human plasma assay contains 5% fetal bovine serum
[b]Number of independent replicates

TABLE 3

Antiviral Activity of Compound 1 in the HCV Subgenomic Stable Replicon Cell Culture Assay

| HCV Replicon Subtype | N[b] | 40% Human Plasma[a] Mean EC$_{50}$, nM, ± Std. Dev. |
|---|---|---|
| Genotype 1a | 10 | 5.3 ± 1.0 |
| Genotype 1b | 8 | 10 ± 5.0 |

[a]The 0% human plasma assay contains 5% fetal bovine serum
[b]Number of independent replicates When tested against common HCV genotype 1 NS3 resistance-associated variants, such as V36M, R155K, D168A and D168V in GT 1a (H77), or T54A, R155K, D168V and V170A in GT 1b (Con-1), Compound 1 showed inhibitory activity nearly equivalent to that against wild-type HCV replicon. Compound 1 was also shown to have potent activity against many NS5A inhibitor and NS5B inhibitor resistance-associated variants in vitro (e.g., M28T, M28V, Q30D, Q30R, Y93C, Y93H, Y93N, L31V+Y93H, C316Y, M414T, Y448C, Y448H, S556G and S559G in GT 1a, and L28T, Y93H, S282T, C316Y, Y448H and S556G in GT 1b).

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A method for treatment of a patient infected with hepatitis C virus (HCV), comprising administering at least two direct acting antiviral agents (DAAs) to said patient, wherein said treatment does not include administration of either interferon or ribavirin to said patient, and said treatment lasts for 8, 9, 10, 11 or 12 weeks, and wherein said at least two DAAs comprise (1) Compound 1

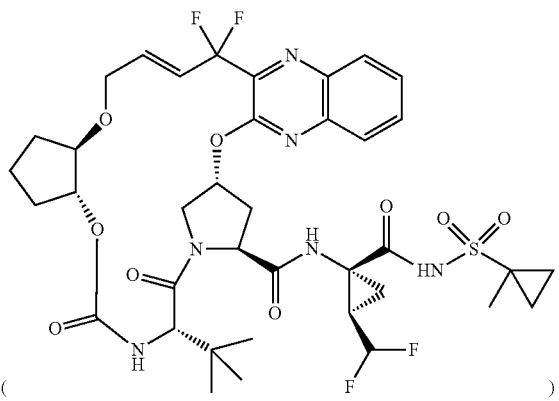

or a pharmaceutically acceptable salt thereof and (2) Compound 2

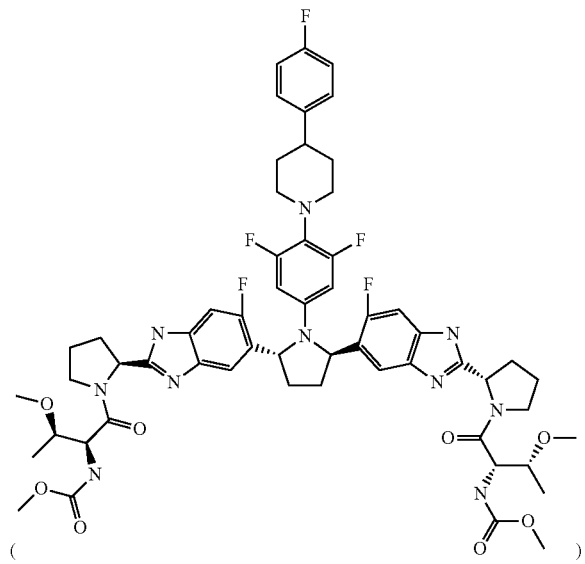

or a pharmaceutically acceptable salt thereof.

2. The method of claim 1, wherein said treatment lasts for 12 weeks.

3. The method of claim 1, wherein said treatment lasts for 10 weeks.

4. The method of claim 1, wherein said treatment lasts for 8 weeks.

5. The method of claim 1, wherein said patient is infected with HCV genotype 1.

6. The method of claim 1, wherein said patient is infected with HCV genotype 2.

7. The method of claim 1, wherein said patient is infected with HCV genotype 3.

8. The method of claim 1, wherein said patient is without cirrhosis.

9. The method of claim 1, wherein said patient is with compensated cirrhosis.

10. The method of claim 1, wherein said patient is a treatment-naive patient.

11. The method of claim 1, wherein said patient is a treatment-experienced patient.

12. The method of claim 1, wherein said at least two DAAs consist of (1) Compound 1 or a pharmaceutically acceptable salt thereof and (2) Compound 2 or a pharmaceutically acceptable salt thereof.

13. The method of claim 12, wherein said treatment lasts for 12 weeks.

14. The method of claim 12, wherein said treatment lasts for 8 weeks.

15. The method of claim 12, wherein said patient is infected with HCV genotype 1.

16. The method of claim 12, wherein said patient is infected with HCV genotype 2.

17. The method of claim 12, wherein said patient is infected with HCV genotype 3.

18. The method of claim 12, wherein said patient is a treatment-naive patient without cirrhosis.

19. The method of claim 12, wherein said patient is a treatment-naive patient with compensated cirrhosis.

20. The method of claim 12, wherein said patient is a treatment-experienced patient without cirrhosis.

21. The method of claim 12, wherein said patient is a treatment-experienced patient with compensated cirrhosis.

22. The method of claim 12, wherein said at least two DAAs consist of Compound 1 and Compound 2, and wherein Compound 1 is administered once daily to said patient, and Compound 2 is administered 120 mg once daily to said patient.

23. The method of claim 22, wherein said patient is infected with HCV genotype 1.

24. The method of claim 22, wherein said patient is infected with HCV genotype 2.

25. The method of claim 22, wherein said patient is infected with HCV genotype 3.

26. The method of claim 22, wherein said patient is infected with HCV genotype 4.

27. The method of claim 22, wherein said patient is infected with HCV genotype 5.

28. The method of claim 22, wherein said patient is infected with HCV genotype 6.

29. A method for treatment of a patient infected with HCV, comprising administering at least two direct acting antiviral agents (DAAs) to said patient, wherein said treatment does not include administration of either interferon or ribavirin to said patient, and said treatment lasts for 16 weeks, and wherein said at least two DAAs comprise (1) Compound 1 or a pharmaceutically acceptable salt thereof and (2) Compound 2 or a pharmaceutically acceptable salt thereof.

30. The method of claim 29, wherein said at least two DAAs consist of Compound 1 and Compound 2 each of which is administered to said patient once daily.

31. The method of claim 30, wherein said Compound 2 is administered 120 mg once daily to said patient.

32. The method of claim 31, wherein said patient is without cirrhosis.

33. The method of claim 31, wherein said patient is with compensated cirrhosis.

34. The method of claim 31, wherein said patient is a treatment-experienced patient.

* * * * *